US010261065B2

(12) United States Patent
Ramsey et al.

(10) Patent No.: US 10,261,065 B2
(45) Date of Patent: Apr. 16, 2019

(54) NANOFLUIDIC DEVICES WITH INTEGRATED COMPONENTS FOR THE CONTROLLED CAPTURE, TRAPPING, AND TRANSPORT OF MACROMOLECULES AND RELATED METHODS OF ANALYSIS

(71) Applicant: The University of North Carolina at Chapel Hill, Chapel Hill, NC (US)

(72) Inventors: John Michael Ramsey, Chapel Hill, NC (US); Laurent Menard, Cary, NC (US)

(73) Assignee: The University of North Carolina at Chapel Hill, Chapel Hill, NC (US)

( * ) Notice: Subject to any disclaimer, the term of this patent is extended or adjusted under 35 U.S.C. 154(b) by 331 days.

(21) Appl. No.: 14/190,520

(22) Filed: Feb. 26, 2014

(65) Prior Publication Data

US 2014/0238856 A1   Aug. 28, 2014

Related U.S. Application Data

(60) Provisional application No. 61/770,586, filed on Feb. 28, 2013.

(51) Int. Cl.
*C25D 21/12*   (2006.01)
*G01N 33/487*   (2006.01)
(Continued)

(52) U.S. Cl.
CPC .. *G01N 33/48721* (2013.01); *B01L 3/502761* (2013.01); *B01L 3/502707* (2013.01); *B01L 2200/0663* (2013.01); *B01L 2300/0896* (2013.01); *B01L 2400/0415* (2013.01); *G01N 27/44791* (2013.01)

(58) Field of Classification Search
USPC ............ 204/228.1, 406, 452, 453, 601, 604; 422/501–504, 518; 436/94, 180
See application file for complete search history.

(56) References Cited

U.S. PATENT DOCUMENTS

| 5,858,187 A | 1/1999 | Ramsey et al. |
|---|---|---|
| 5,872,010 A | 2/1999 | Karger et al. |

(Continued)

FOREIGN PATENT DOCUMENTS

| JP | 2003-166934 A | 6/2003 |
|---|---|---|
| JP | 2005-102619 | 4/2005 |

(Continued)

OTHER PUBLICATIONS

Alkan et al., "Genome structural variation discovery and genotyping", *Nat. Rev. Genet.*, 2011, vol. 12, pp. 363-376.
(Continued)

*Primary Examiner* — Dean Kwak
(74) *Attorney, Agent, or Firm* — Myers Bigel, P.A.

(57) ABSTRACT

Devices for controlling the capture, trapping, and transport of macromolecules include at least one fluidic transport nanochannel that intersects and is in fluid communication with at least one transverse nanochannel with (shallow) regions and/or with integrated transverse electrodes that enable fine control of molecule transport dynamics and facilitates analyses of interest, e.g., molecular identification, length determination, localized (probe) mapping and the like.

11 Claims, 11 Drawing Sheets

(51) Int. Cl.
*B01L 3/00* (2006.01)
*G01N 27/447* (2006.01)

(56) References Cited

U.S. PATENT DOCUMENTS

| | | |
|---|---|---|
| 6,524,456 B1 | 2/2003 | Ramsey et al. |
| 6,790,671 B1 | 9/2004 | Austin et al. |
| 6,803,568 B2 | 10/2004 | Luc et al. |
| 7,033,474 B1 | 4/2006 | Dubrow et al. |
| 7,465,381 B2 | 12/2008 | Lopez et al. |
| 7,670,770 B2 | 3/2010 | Chou et al. |
| 7,744,762 B2 | 6/2010 | Lazar |
| 7,960,105 B2 | 6/2011 | Schwartz et al. |
| 8,246,799 B2 | 8/2012 | Oliver et al. |
| 8,333,934 B2 | 12/2012 | Cao et al. |
| 8,722,327 B2 | 5/2014 | Cao et al. |
| 8,735,065 B2 | 5/2014 | Craighead et al. |
| 8,764,968 B2 * | 7/2014 | Afzali-Ardakani .......... G01N 33/48721 204/403.01 |
| 9,061,901 B2 | 6/2015 | Cao et al. |
| 2002/0000516 A1 | 1/2002 | Schultz et al. |
| 2002/0061529 A1 | 5/2002 | Bridgham et al. |
| 2002/0072243 A1 | 6/2002 | Craighead et al. |
| 2002/0081744 A1 | 6/2002 | Chan et al. |
| 2002/0160365 A1 | 10/2002 | O'Brien |
| 2002/0190204 A1 | 12/2002 | Hofstadler et al. |
| 2002/0197603 A1 * | 12/2002 | Chow .................. B01L 3/5027 435/6.19 |
| 2003/0146377 A1 | 8/2003 | Miller et al. |
| 2004/0033515 A1 | 2/2004 | Cao et al. |
| 2004/0166504 A1 | 8/2004 | Rossier et al. |
| 2005/0023156 A1 | 2/2005 | Ramsey et al. |
| 2005/0082204 A1 | 4/2005 | Schwartz et al. |
| 2005/0103713 A1 | 5/2005 | Ramsey et al. |
| 2005/0196746 A1 | 9/2005 | Xu et al. |
| 2006/0084078 A1 | 4/2006 | Zhao |
| 2006/0169587 A1 | 8/2006 | Lopez et al. |
| 2006/0240573 A1 | 10/2006 | Kao et al. |
| 2006/0275778 A1 | 12/2006 | Wu et al. |
| 2006/0278879 A1 | 12/2006 | Busta |
| 2007/0057179 A1 | 3/2007 | Bousse et al. |
| 2007/0145263 A1 | 6/2007 | Weng |
| 2007/0192911 A1 | 8/2007 | Jin et al. |
| 2008/0057192 A1 | 3/2008 | Faguet |
| 2009/0023146 A1 | 1/2009 | Harnack et al. |
| 2009/0111115 A1 | 4/2009 | Drmanac et al. |
| 2009/0115094 A1 | 5/2009 | Chou et al. |
| 2009/0136682 A1 | 5/2009 | Branton et al. |
| 2009/0305273 A1 | 12/2009 | Cao et al. |
| 2010/0029508 A1 | 2/2010 | Austin et al. |
| 2010/0075428 A1 | 3/2010 | Wang et al. |
| 2010/0159462 A1 | 6/2010 | Takayama et al. |
| 2011/0036994 A1 | 2/2011 | Frayling |
| 2011/0201509 A1 | 8/2011 | Tegenfeldt et al. |
| 2011/0226623 A1 | 9/2011 | Timp et al. |
| 2011/0227558 A1 | 9/2011 | Mannion et al. |
| 2011/0296903 A1 * | 12/2011 | Cao .................. B01L 3/502761 73/64.56 |
| 2011/0308949 A1 | 12/2011 | Afzali-Ardakani et al. |
| 2012/0193231 A1 | 8/2012 | Afzali-Ardakani et al. |
| 2012/0196376 A1 | 8/2012 | Park et al. |
| 2013/0068618 A1 | 3/2013 | Harrer et al. |
| 2013/0195723 A1 | 8/2013 | Ramsey et al. |
| 2013/0224736 A1 | 8/2013 | Marie et al. |
| 2014/0194313 A1 | 7/2014 | Craighead et al. |
| 2014/0194314 A1 | 7/2014 | Walsworth et al. |
| 2014/0197105 A1 | 7/2014 | DiBiasio et al. |
| 2014/0234980 A1 * | 8/2014 | Ramsey ........... G01N 27/44791 436/94 |
| 2014/0272958 A1 | 9/2014 | Ramsey et al. |
| 2015/0008124 A1 | 1/2015 | Oliver |

FOREIGN PATENT DOCUMENTS

| | | |
|---|---|---|
| JP | 2007-149861 | 6/2007 |
| WO | WO 96/04547 A1 | 2/1996 |
| WO | WO 2000/002038 A1 | 1/2000 |
| WO | WO 01/13088 A1 | 2/2001 |
| WO | WO 03/025540 A2 | 3/2003 |
| WO | WO 2007/011622 A2 | 1/2007 |
| WO | WO 2008/079169 A2 | 7/2008 |
| WO | WO 2008/132734 A2 | 11/2008 |
| WO | WO 2009/030953 A1 | 3/2009 |
| WO | WO 2009/120642 | 10/2009 |
| WO | WO 2012/040098 A2 | 3/2012 |
| WO | WO 2012/055415 A1 | 5/2012 |
| WO | WO 2013/039778 | 3/2013 |
| WO | WO 2013/088098 A2 | 6/2013 |
| WO | WO 2013/119765 A1 | 8/2013 |
| WO | WO 2013/176767 A1 | 11/2013 |
| WO | WO 2013/191908 A1 | 12/2013 |

OTHER PUBLICATIONS

Baday et al., "Multicolor super-resolution DNA imaging for genetic analysis", *Nano Lett.*, 2012, vol. 12, pp. 3861-3866.

Balducci et al., "Conformational preconditioning by electrophoresis of DNA through a finite obstacle array", *Macromolecules*, 2008, vol. 41, pp. 5485-5492.

Brochard-Wyart et al., "Dynamics of Taut DNA chains", *Europhys. Lett.*, 1999, vol. 47(2), pp. 171-174.

Chantiwas et al., "Flexible fabrication and applications of polymer nanochannels and nanoslits", *Chem. Soc. Rev.*, 2011, vol. 40, pp. 3677-3702.

Chou et al., "A microfabricated device for sizing and sorting DNA molecules", *Proc. Natl. Acad. Sci.*, 1999, vol. 96, pp. 11-13.

Craddock et al., "Genome-wide association study of CNVs in 16,000 cases of eight common diseases and 3,000 shared controls", *Nature*, 2010, vol. 464, pp. 713-720.

Craighead et al. "Future lab-on-a-chip technologies for interrogating individual molecules" Nature 2006, 442, 387.

Das et al., "Single molecule linear analysis of DNA in nano-channel labeled with sequence specific fluorescent probes", *Nucl. Acids Res.*, 2010, vol. 38, e177, 8 pages.

Dimalanta et al., "A microfluidic system for large DNA molecule arrays", *Anal. Chem.*, 2004, vol. 76, pp. 5293-5301.

Duke et al. "Microchips for Sorting DNA" pp. 11-26, 1997.

Eijkel et al. "Nanofluidics: what is it and what can we expect from it?" Microfluid. Nanofluid. 2005, 1, 249.

Fischbein et al. "Sub-10 nm Device Fabrication in a Transmission Electron Microscope" Nano Letters 2007, vol. 7, 1329.

Foquet et al., "DNA fragment sizing by single molecule detection in submicrometer-sized closed fluidic channels", *Anal. Chem.*, 2002, vol. 74, pp. 1415-1422.

Freitag et al., "Meandering nanochannels for imaging of ultra-long DNA molecules", *Proceedings of the 15th International Conference on Miniaturized Systems for Chemistry and Life Sciences*, Oct. 2-6, 2011, Seattle, Washington; Landers, J. P., Herr, A., Juncker, D., Pamme, N., Bienvenue, J., Eds.; The Printing House: Stoughton, WI, 2011, pp. 1758-1760.

Gierhart et al. "Nanopore with transverse nanoelectrodes for electrical characterization and sequencing of DNA" Sens. and Actuators B 2008, 132, 593.

Jo et al., "A single-molecule barcoding system using nanoslits for DNA analysis", *Proc. Natl. Acad. Sci.*, 2007, vol. 104, No. 8, pp. 2673-2678.

Kim et al., "A highly annotated whole-genome sequence of a Korean individual", *Nature*, 2009, vol. 460, pp. 1011-1015.

Lerman et al., Communications to the Editor "Why Does the Electrophoretic Mobility of DNA in Gels Vary with the Length of the Molecule?" Biopolymers 1982, 21, 995-997.

Levy et al. "Entropic Unfolding of DNA Molecules in Nanofluidic Channels" Nano Letters, 2008, 8, 3839.

Li et al. "Sacrificial polymers for nanofluidic channels in biological applications" Nanotechnology 2003, 14, 578.

(56) References Cited

OTHER PUBLICATIONS

Liang et al. "Single Sub-20 nm Wide, Centimeter-Long Nanofluidic Channel Fabricated by Novel Nanoimprint Mold Fabrication and Direct Imprinting", Nano Letters, 2007, vol. 7, 3774.
Lim et al., "DNA methylation profiling in nanochannels", *Biomicrofluidics*, 2011, vol. 5, 034106, 9 pages.
Mannion et al., "Conformational analysis of single DNA molecules undergoing entropically induced motion in nanochannels", *Biophys. J.*, 2006, vol. 90, pp. 4538-4545.
Mao et al. "Fabrication and characterization of 20 nm planar nanofluidic channels by glass-glass and glass-silicon bonding" Lab Chip 2005, 5, 837.
Marie et al. "Nanofluidic devices towards single DNA molecule sequence mapping", *Journal of Biophotonics*, 2012, pp. 673-686, vol. 5, No. 8-9.
Mark et al., "Microfluidic lab-on-a-chip platforms: requirements, characteristics and applications", *Chem. Soc. Rev.*, 2010, vol. 39, pp. 1153-1182.
McCarroll et al., "Copy-number variation and association studies of human disease", *Nat. Genet.*, 2007, vol. 39, pp. S37-S42.
McCarthy et al., "Microduplications of 16p11.2 are associated with schizophrenia", *Nat. Genet.*, 2009, vol. 41, No. 11, pp. 1223-1227.
Menard et al., "A Device for Performing Lateral Conductance Measurements on Individual Double-Stranded DNA Molecules", *ACS Nano*, 2012, vol. 6(10), pp. 9087-9094.
Menard et al., "Electrokinetically-Driven Transport of DNA Through Focused Ion Beam Milled Nanofluidic Channels", *Anal. Chem.*, 2013, vol. 85, pp. 1146-1153.
Mills et al., "Mapping copy number variation by population-scale genome sequencing", *Nature*, 2011, vol. 470, pp. 59-65.
Pinard et al., "Assessment of whole genome amplification-induced bias through high-throughput, massively parallel whole genome sequencing", *BMC Genomics*, 2006, vol. 7, 216, 21 pages.
Pinkel et al., "Comparative genomic hybridization", *Annu. Rev. Genomics Hum. Genet.*, 2005, vol. 6, pp. 331-354.
Pinto et al., "Functional impact of global rare copy number variation in autism spectrum disorders", *Nature*, 2010, vol. 466, pp. 368-372.
Randall et al., "Methods to electrophoretically stretch DNA: microcontractions, gels, and hybrid gel-microcontraction devices", *Lab Chip*, 2006, vol. 6, pp. 516-525.
Sebat et al., "Strong association of de novo copy number mutations with autism", *Science*, 2007, vol. 316, pp. 445-449.
Smeets et al. "Salt Dependence of Ion Transport and DNA Translocation through Solid State Nanopores" Nano Letters 2006, vol. 6, No. 1, 89.
Smith et al., "Overstretching B-DNA: The elastic response of individual double-stranded and single-stranded DNA molecules", *Science*, 1996, vol. 271, pp. 795-799.
So et al. "Inherently aligned microfluidic electrodes composed of liquid metal", Lab Chip, 2011, 11, 905-911.
Sorek et al., "Genome-wide experimental determination of barriers to horizontal gene transfer", *Science*, 2007, vol. 318, pp. 1449-1452.
Speicher et al., "Effect of genome-wide association studies, direct-to-consumer genetic testing, and high-speed sequencing technologies on predictive genetic counselling for cancer risk", *Lancet Oncol.*, Sep. 2010, vol. 11, pp. 890-898.
Stefansson et al., "Large recurrent microdeletions associated with schizophrenia", *Nature*, 2008, vol. 455, pp. 232-236.
Teague et al., "High-resolution human genome structure by single-molecule analysis", *Proc. Natl. Acad. Sci.*, 2010, vol. 107, pp. 10848-10853.
Topolancik et al., "Extraction and purification of genomic DNA via entrapment in an array of microposts", *Proceedings of the 15th International Conference on Miniaturized Systems for Chemistry and Life Sciences*, Oct. 2-6, 2011, Seattle, Washington; Landers, J. P., Herr, A., Juncker, D., Pamme, N., Bienvenue, J., Eds.; The Printing House: Stoughton, WI, 2011, p. 1026-1028.
Treangen et al., "Repetitive DNA and next-generation sequencing: computational challenges and solutions", *Nat. Rev. Genet.*, 2011, vol. 13, pp. 36-46.
Tsutsui et al. "Transverse Field Effects on DNA-Sized Particle Dynamics" Nano Letters 2009, vol. 9, No. 4, 1659.
Turner et al., "Confinement-induced entropic recoil of single DNA molecules in a nanofluidic structure", *Phys. Rev. Lett.*, 2002, vol. 88, 128103.
Utko et al., "Injection molded nanofluidic chips: Fabrication method and functional tests using single-molecule DNA experiments", *Lab Chip*, 2011, vol. 11, pp. 303-308.
Zhou et al., "A single molecule system for whole genome analysis", *Perspectives in Bioanalysis, vol. 2, New High Throughput Technologies for DNA Sequencing and Genomics*; Mitchelson, K. R., Ed.; 2007, Elsevier: Amsterdam; pp. 265-300.
Zhou et al., "A whole-genome shotgun optical map of Yersinia pestis strain KIM", *Appl. Environ. Microbiol.*, 2002, vol. 68, No. 12, pp. 6321-6331.
Zhou et al., "Whole-genome shotgun optical mapping of Rhodobacter sphaeroides strain 2.4.1 and its use for whole-genome shotgun sequence assembly", *Genome Res.*, 2003, vol. 13, pp. 2142-2151.
Abgrall et al., "Nanofluidic Devices and Their Applications", *Anal. Chem.*, 2008, vol. 80, pp. 2326-2341.
Apel et al., "Diode-like single-ion track membrane prepared by electro-stopping", *Nucl. Instrum. Methods Phys. Res.*, Sect. B, 2001, 184, 337-346.
Balducci et al., "Double-Stranded DNA Diffusion in Slitlike Nanochannels", *Macromolecules*, 2006, vol. 39, pp. 6273-6281.
Brochard et al., "Dynamics of confined polymer chains", J. Chem. Phys., Jul. 1977, vol. 67, pp. 52-56.
Campbell et al. "Electrophoretic manipulation of single DNA molecules in nanofabricated capillaries", *Lab Chip*, 2004, 4:225-229.
Cao et al. "Fabrication of 10 nm enclosed nanofluidic channels", *Applied Physics Letters*, vol. 81, No. 1, Jul. 2002, pp. 174-176.
Cao et al., "Gradient nanostructures for interfacing microfluidics and nanofluidics", *Appl. Phys. Lett.*, Oct. 14, 2002; vol. 81, No. 16, pp. 3058-3060.
Cipriany et al., "Single molecule epigenetic analysis in a nanofluidic channel", Anal. Chem., Mar. 15, 2010, vol. 82, No. 6, pp. 2480-2487.
Cross et al. "Size-dependent DNA mobility in nanochannels", *Journal of Applied Physics*, 2007, vol. 102, pp. 024701-1-024701-5.
Cui, S.T., "Counterion-Hopping along the Backbone of Single-Stranded DNA in Nanometer Pores: A Mechanism for Current Conduction", *Physical Review Letters*, 2007, vol. 98, pp. 138101-1-138101-4.
Douville et al., "DNA linearization through confinement in nanofluidic channels", *Anal Bioanal Chem.*, 2008, vol. 391, pp. 2395-2409.
Fan et al. "DNA Translocation in Inorganic Nanotubes", *Nano Letters*, vol. 5, No. 9, Sep. 2005, 1633-1637.
Gierak et al. "Sub-5 nm FIB direct patterning of nanodevices", *Microelectronic Engineering*, 2007, vol. 84, pp. 779-783.
Han et al., "Prediction of nanopattern topography using two-dimensional focused ion beam milling with beam irradiation intervals", *Microelectronic Engineering*, 2010, vol. 87, pp. 1-9.
Han et al., "Separation of long DNA molecules in a microfabricated entropic trap Array", *Science*, May 12, 2000; vol. 288, No. 5468, pp. 1026-1029.
Haneveld et al., "Wet anisotropic etching for fluidic 1D nanochannels", *J. Micromech. Microeng.*, 2003, vol. 13, pp. S62-S66.
Holzer et al., "Three-dimensional analysis of porous $BaTiO_3$ ceramics using FIB nanotomography", *Journal of Microscopy*, vol. 216, Pt. 1, Oct. 2004, pp. 84-95.
Huh et al., "Tuneable elastomeric nanochannels for nanofluidic manipulation", *Nature Materials*, vol. 6, Jun. 2007, pp. 424-428.
Kasianowicz et al., "Nanoscopic Porous Sensors", *Annu. Rev. Anal. Chem.*, 2008, vol. 1, pp. 737-766.
Kim et al., "Design and numerical simulation of a DNA electrophoretic stretching device", *Lab Chip*, 2007, vol. 7, pp. 213-215.
Kovarik et al., "Nanofluidics in Lab-on-a-Chip Devices", *Anal. Chem.*, 2009, vol. 81, No. 17, pp. 7133-7140.
Kumar et al., "Origin of translocation barriers for polyelectrolyte chains", J. Chem. Phys. 2009, vol. 131, pp. 194903-1-194903-18.
Lagerqvist et al. "Fast DNA Sequencing via Transverse Electronic Transport", *Nano Letters*, 2006, vol. 6, No. 4, pp. 779-782.

(56) References Cited

OTHER PUBLICATIONS

Lam et al., "Genome mapping on nanochannel arrays for structural variation analysis and sequence assembly", *Nat. Biotech.*, Aug. 2012, vol. 30, No. 8, pp. 771-776.
Larson et al., "Single DNA molecule stretching in sudden mixed shear and elongational microflows", *Lab Chip*, 2006, vol. 6, Issue 9, pp. 1187-1199.
Lerman et al. "Why Does the Electrophoretic Mobility of DNA in Gels Vary with the Length of the Molecule?", *Biopolymers*, 1982, vol. 21, pp. 995-997.
Levy et al., "DNA manipulation, sorting, and mapping in nanofluidic systems", Chem Soc Rev 2010; vol. 39, Issue 3, pp. 1133-1152.
Li et al., "Focused ion beam fabrication of silicon print masters", *Nanotechnology*, 2003, vol. 14, pp. 220-223.
Liang et al., "Nanogap detector inside nanofluidic channel for fast real-time label-free DNA analysis", *Nano Letters*, 2008, vol. 8, No. 5, pp. 1472-1476.
Lugstein et al., "FIB processing of silicon in the nanoscale regime", *Applied Physics A*, 2003, vol. 76, pp. 545-548.
Maleki et al., "A nanofluidic channel with embedded transverse nanoelectrodes", *Nanotechnology*, 2009, vol. 20:105302, pp. 1-6.
Menard et al., "Analysis of Single DNA Molecules Translocating Through Nanochannels Fabricated in $SiO_2$", *Twelfth International Conference on Miniaturized Systems for Chemistry and Life Sciences*, Oct. 12-16, 2008, San Diego, California, 4 pages.
Menard et al., "Fabrication of Sub-5 nm Nanochannels in Insulating Substrates Using Focused Ion Beam Milling", *Nano Letters*, 2011, vol. 11, No. 2, pp. 512-517.
Menard, Jr. et al., "DNA Transport Characteristics in Focused Beam-Milled Nanofluidic Devices", *2009 Annual Meeting of the American Electrophoresis Society (AES)*, Nov. 10, 2009, Retrieved from the internet at URL http://aiche.confex.com/aiche/2009/webprogram/Paaper160572.html.
Mijatovic et al., "Technologies for nanofluidic systems: *top-down* vs. *bottom-up*—a review", *Lab Chip*, 2005, vol. 5, pp. 492-500.
Nakayama et al., "Stability and Schottky barrier of silicides: First-principles study", *Microelectronic Engineering*, 2009, vol. 86, pp. 1718-1721.
Nikoobakht, B., "A Scalable Platform for Integrating Horizontal Nanochannels with Known Registries to Microchannels", *Chem. Mater.*, 2009, vol. 21, pp. 27-32.
Orloff et al., "Fundamental limits to imaging resolution for focused ion beams", *Journal of Vacuum Science & Technology B*, Nov./Dec. 1996, vol. 14, No. 6, pp. 3759-3763.
Perry et al., "Ion transport in nanofluidic funnels", *ACS Nano*, 2010, vol. 4, No. 7, pp. 3897-3902.
Perry et al., "Review of fabrication of nanochannels for single phase liquid flow", *Microfluid Nanofluid*, 2006, vol. 2, pp. 185-193.
Persson et al., "Confinement spectroscopy: probing single DNA molecules with tapered nanochannels", *Nano Letters*, 2009, vol. 9, No. 4, pp. 1382-1385.
Randolph et al., "Focused, Nanoscale Electron-Beam-Induced Deposition and Etching", *Critical Reviews in Solid State and Materials Sciences*, , 2006, 31:3, pp. 55-89.
Reccius et al., "Conformation, length, and speed measurements of electrodynamically stretched DNA in nanochannels", *Biophys. J.*, Jul. 2008, vol. 95, pp. 273-286.
Reisner et al., "DNA confinement in nanochannels: physics and biological applications", *Rep. Prog. Phys.*, 2012, vol. 75, Issue 10, 106601, 35 pages.
Reisner et al., "Nanoconfinement-Enhanced Conformational Response of Single DNA Molecules to Changes in Ionic Environment", *Physical Review Letters*, 2007, vol. 99, pp. 058302-1-058302-4.
Reisner et al., "Single-molecule denaturation mapping of DNA in nanofluidic channels", *Proc. Natl. Acad. Sci.*, Jul. 27, 2010; vol. 107, Issue 30, pp. 13294-13299.
Reisner et al., "Statics and Dynamics of Single DNA Molecules Confined in Nanochannels", *Physical Review Letters*, 2005, vol. 94, pp. 196101-1-196101-4.

Riehn et al., "Restriction mapping in nanofluidic devices", *PNAS*, Jul. 19, 2005; vol. 102, No. 29, pp. 10012-10016.
Salieb-Beugelaar et al., "Electrophoretic separation of DNA in gels and nanostructures", *Lab Chip*, 2009, vol. 9, pp. 2508-2523.
Salieb-Beugelaar et al., "Field-Dependent DNA Mobility in 20 nm High Nanoslits", *Nano Letters*, Jul. 2008, vol. 8, No. 7, pp. 1785-1790.
Schoch, R.B., "Transport phenomena in nanofluidics", *Reviews of Modern Physics*, vol. 80, No. 3, Jul.-Sep. 2008, pp. 839-883.
Stavis et al., "Nanofluidic structures with complex three-dimensional surfaces", *Nanotechnology*, 2009, vol. 20, Issue 16, 165302, 7 pages.
Striemer et al., "Charge- and size-based separation of macromolecules using ultrathin silicon membranes", *Nature*, Feb. 15, 2007; vol. 445, pp. 749-753.
Strychalski et al., "Diffusion of DNA in Nanoslits", *Macromolecules*, 2008, vol. 41, pp. 7716-7721.
Strychalski et al., "Non-planar nanofluidic devices for single molecule analysis fabricated using nanoglassblowing",*Nanotechnology*, 2008, vol. 19, Issue 16, 315301, 8 pages.
Taniguchi et al., Fabrication of the gating nanopore device, *Applied Physics Letters*, 2009, vol. 95, pp. 123701-1-123701-3.
Tegenfeldt et al., "The dynamics of genomic-length DNA molecules in 100-nm Channels", *Proc. Natl. Acad. Sci.*, Jul. 27, 2004; vol. 101, No. 30, pp. 10979-10983.
Tong et al., "Silicon Nitride Nanosieve Membrane", *Nano Letters*, 2004, vol. 4, No. 2, pp. 283-287.
Tseng, A., "Recent developments in micromilling using focused ion beam technology", *J. Micromech. Microeng.*, 2004, vol. 14, pp. R15-R34.
Volkmuth et al., "DNA electrophoresis in microlithographic arrays", *Nature*, Aug. 13, 1992; vol. 358, pp. 600-602.
Wang et al., "Manipulating DNA molecules in nanofluidic channels", *Microfluid Nanofluid*, 2006, vol. 2, pp. 85-88.
Wang et al., "Single-molecule studies of repressor-DNA interactions show long-range interactions", *PNAS*, Jul. 12, 2005; vol. 102, No. 28, pp. 9796-9801.
Xu et al., "Wide-spectrum, ultrasensitive fluidic sensors with amplification from both fluidic circuits and metal oxide semiconductor field effect transistors", *Applied Physics Letters*, 2007, vol. 91, pp. 013901-1-013901-3.
Yuan et al., "Electrokinetic transport and separations in fluidic nanochannels", *Electrophoresis*, 2007, vol. 28, pp. 595-610.
Zangle et al., "Theory and experiments of concentration polarization and ion focusing at microchannel and nanochannel interfaces", *Chem. Soc. Rev.*, 2010, vol. 39, pp. 1014-1035.
Zwolak, M., "Electronic Signature of DNA Nucleotides via Transverse Transport", *Nano Letters*, 2005, vol. 5, No. 3, pp. 421-424.
International Search Report and Written Opinion for related PCT Application No. PCT/US2014/018488, dated Jun. 16, 2014.
Gierhart et al., Nanopore with traverse nanoelectrodes for electrical characterization and sequencing of DNA, Sensors and Actuators B, 2008, pp. 593-600, vol. 132.
Pang et al., Fixed-Gap Tunnel Junction for Reading DNA Nucleotides, ACSNANO, 2014, pp. 11994-12003, vol. 8, No. 12.
Reisner et al., DNA confinement in nanochannels: physics and biological applications, Reports on Progress in Physics, 2012, pp. 1-34, vol. 75, 106601.
Wanunu, Nanopores: A journey towards DNA sequencing, Physics of Life Reviews, 2012, pp. 125-158, vol. 9.
Zhu et al., Arrays of horizontally-oriented mini-reservoirs generate steady microfluidic flows for continuous perfusion cell culture and gradient generation, The Royal Society of Chemistry, 2004, pp. 1026-1031, vol. 129.
Ai et al. "Field Effect Regulation of DNA Translocation through a Nanopore" *Analytical Chemistry* 82(19):8217-8225 (2010).
Allison et al. "Direct atomic force microscope imaging of EcoRI endonuclease site specifically bound to plasmid DNA molecules" *Proceedings of the National Academy of Sciences*, USA 93:8826-8829 (1996).
Jo et al. "Elongation and Migration of Single DNA Molecules in Microchannels Using Oscillatory Shear Flows" *Lap Chip* 9(16):2348-2355 (2009).

(56) References Cited

OTHER PUBLICATIONS

Viero et al. "Hydrodynamic Manipulation of DNA in Nanopost Arrays: Unhooking Dynamics and Size Separation" *Small* 7(24):3508-3518 (2011).
Zhou et al. "Transport and Sensing in Nanofluidic Devices" *Annual Review of Analytical Chemistry* 4:321-341 (2011).

* cited by examiner

NANOFLUIDIC DEVICES WITH INTEGRATED COMPONENTS FOR THE CONTROLLED CAPTURE, TRAPPING, AND TRANSPORT OF MACROMOLECULES AND RELATED METHODS OF ANALYSIS

RELATED APPLICATIONS

This application claims the benefit of and priority to U.S. Provisional Application Ser. No. 61/770,586, filed Feb. 28, 2013, the contents of which are hereby incorporated by reference as if recited in full herein.

STATEMENT OF FEDERAL SUPPORT

This invention was made with government support under Grant No. HG002647 awarded by the National Institutes of Health. The government has certain rights in the invention.

FIELD OF THE INVENTION

This invention relates to detection/characterization and/or measurement of molecules using fluidics and nanochannels.

BACKGROUND OF THE INVENTION

There has been considerable recent interest in the incorporation of nanoscale components in lab-on-a-chip fluidic devices. This interest owes its origin to several advantages (and differences that may be advantageously leveraged) in moving from the micron scale to the nanoscale. These differences include, for example, double-layer overlap (DLO) and its effect on electro-osmosis and charge permselectivity, localized enhancement of electric fields, higher surface to volume ratios, confinement effects on large synthetic and bio-polymers, and the emerging importance of entropic effects. See, e.g., Yuan et al., *Electrophoresis* 2007, 28, 595-610; Schoch et al., *Rev. Mod. Phys.* 2008, 80, 839-883; and Kovarik et al., *Anal. Chem.* 2009, 81, 7133-7140. Historic examples of nanoscale devices include the use of porous media and gels in chromatographic separations and filtration membranes with nanoscale pores. See, e.g., Lerman et al., *Biopolymers* 1982, 21, 995-997; and Tong et al., M. *Nano Lett.* 2004, 4, 283-287. Recent efforts, however, have been focused on engineering geometrically well-defined conduits for fluid and analyte transport and seamlessly integrating them into devices. See, e.g., Volkmuth et al., *Nature* 1992, 358, 600-602; and Striemer et al., *Nature* 2007, 445, 749-753. The advantage of such regular structures is the relative simplicity of pressure and field gradients, fluid flow, and molecular motion contained within, in contrast to these properties in more tortuous networks. The capability to define, characterize, and easily model these systems can allow a better understanding of separation mechanisms and single molecule physics, for example. See, e.g., Volkmuth et al., *Nature* 1992, 358, 600-602; Reisner et al., *Phys. Rev. Lett.* 2005, 94, 196101; and Salieb-Beugelaar et al., *Lab Chip* 2009, 9, 2508-2523.

Recently FIB milling techniques have been described to form nanofluidic devices. See, Menard et al., Fabrication of Sub-5 nm Nanochannels in Insulating Substrates Using Focused Ion Beam Milling, Nano Lett. 2011, 11, 512-517 (published Dec. 20, 2010); and U.S. Provisional Patent Application Ser. No. 61/384,738, filed Sep. 21, 2010 (and related PCT Application PCT/US2011/052127), entitled, Methods, Systems And Devices For Forming Nanochannels, the contents of which are hereby incorporated by reference as if recited in full herein. In addition to FIB milling, a variety of other methods suitable for nanochannel fabrication can be used, including, for example, electron beam lithography, nanoimprint lithography, photolithography, templating or molding strategies, and other methods understood by one of ordinary skill in the art.

A number of nanofluidic devices have been proposed, including those with integrated miniature electrodes (nano- or micro-scale) for single-molecule sensing and/or nucleic acid sequencing. The incorporation of the electrodes as a device component can require difficult fabrications and small differences in electrode geometry may result in high device-to-device variability. In addition, fluorescence-based systems can have limited temporal resolution, typically about 400 frames or less per second, and may require relatively bulky and/or expensive optics and imaging components. There remains a need for alternate device designs and/or evaluation techniques.

SUMMARY OF EMBODIMENTS OF THE INVENTION

Embodiments of the invention are configured to provide devices that facilitate capture, trapping and transport through a nanochannel having critical dimensions smaller than the radius of gyration of a molecule (macromolecule) under analysis using electrokinetic control of a respective nanochannel with significantly different electric filed strength segments and/or using concentration polarization to thereby allow the capture of very large macromolecules with reduced incidence of fragmentation.

Embodiments of the invention provide devices that drive DNA to the nanochannel entrance of the transport channel very quickly and apply enough force on the molecule to overcome the entropic barrier for threading into the nanochannel. The DNA can transport rapidly through the first part of the nanochannel but then experience a reduction in velocity at the intersection with transverse electrodes or nanofluidic elements.

Embodiments of the invention provide devices, such as chips for DNA analysis, that have at least one fluid transport nanochannel with at least one nanochannel with shallow regions adjacent and in fluid communication with the transport nanochannel and/or with integrated electrodes to determine characteristics or parameters of interest, e.g., molecular identification, length determination, localized (probe) mapping and the like.

Embodiments of the invention are directed to nanofluidic analysis devices. The devices include at least one fluid transport nanochannel and at least one fluid nanochannel with two shallow segments on opposing sides of the fluid transport nanochannel segment at an intersection that resides a distance between end portions of the at least one fluid transport nanochannel to define a first segment and second segment of a respective fluid transport nanochannel. The devices also include first and second electrodes in communication with respective shallow segments, a first electrode in communication with an entry end portion of the fluid transport nanochannel, a second electrode in communication with an egress end portion of the fluid transport nanochannel and a circuit configured to control operation of the electrodes to controllably inject, trap and transport macromolecules. In operation, the first and second segments can have significantly different field strengths to thereby trap a macromolecule so that the macromolecule is at equilibrium or moves with a low velocity.

The shallow segments can merge into deeper segments and can be orthogonal to the fluid transport nanochannel.

The shallow segments can merge into deeper segments and can be parallel to the fluid transport channel.

The device can include a cover sealed to a substrate to define a fluidic analysis chip and a molecule of DNA, RNA, peptide, protein, or other biological or synthetic macromolecule in the at least one fluid transport nanochannel.

Other embodiments are directed to devices having at least one fluid transport nanochannel and two transverse integrated electrodes abutting opposing sides of the at least one fluid transport nanochannel at an intersection with the transport nanochannel that resides a distance between opposing first and second end portions of the at least one transport channel to define a first segment and second segment of the transport nanochannel. In operation, the first and second segments have significantly different field strengths.

The device can include a circuit residing at least partially on the substrate and/or in communication with the substrate configured to selectively apply voltages to the first and second end portions of the fluid transport nanochannel and to the transverse electrodes to generate the significantly different field strength and controllably inject, trap and transport a macromolecule in and through the fluid transport nanochannel.

Still other embodiments are directed to a nanofluidic analysis system. The system includes a device having at least one fluid transport nanochannel having an intersection with either (i) at least one fluid nanochannel with first and second segments facing each other across the fluid transport nanochannel, each in communication with a respective electrode or (ii) two transverse integrated electrodes abutting opposing sides of the at least one fluid transport nanochannel. The intersection resides a distance between opposing end portions of the at least one fluid transport nanochannel to define a first segment and second segment of the respective fluid transport nanochannel. The device also includes a circuit with a power source configured to apply voltages to the electrodes to selectively trap and transport macromolecules through the at least one fluid transport nanochannel.

The device can include the at least one fluid nanochannel with first and second segments facing each other across the fluid transport nanochannel segment, each in communication with a respective electrode, and the first and second segments can be shallow segments.

The first and second segments can be wide segments.

The device can include a plurality of parallel fluid transport nanochannels that cooperate with a respective intersection.

The device can include at least one fluid transport nanochannel with a plurality of longitudinally spaced apart intersections, each intersection having either (i) a fluid nanochannel with first and second segments facing each other across the fluid transport nanochannel, each in communication with a respective electrode or (ii) two transverse integrated electrodes abutting opposing sides of the at least one fluid transport nanochannel.

Still other embodiments are directed to methods of analyzing a macromolecule. The methods include: (a) providing a device with at least one fluidic transport nanochannel that has an intersection that includes either (i) at least one fluid nanochannel with first and second segments facing each other across the fluid transport nanochannel segment in fluid communication with the transport channel, each in communication with a respective electrode or (ii) first and second transverse integrated electrodes abutting opposing sides of the at least one fluid transport nanochannel; (b) electrically applying a bias across the first and second segments or the first and second transverse electrodes to inject or trap a macromolecule in the fluid transport channel; (c) electrically removing all biases causing the macromolecule to relax into an equilibrium conformation; and (d) electrically applying a bias only across the transport nanochannel controlling translocation of the macromolecule through the nanochannel.

The device can include the at least one fluid nanochannel with the first and second segments and the first and second segments can be wide, shallow segments.

The shallow segments can merge into deeper segments and can be orthogonal to the fluid transport nanochannel.

The shallow segments can merge into deeper segments that are parallel to the fluid transport channel.

The device can be a fluidic analysis chip and the macromolecule can be a molecule of DNA, RNA, peptide, protein, or other biological or synthetic macromolecule.

The electrically applying and removing steps can be carried out under the direction of a timing algorithm and/or timing circuit.

The voltage steps can be triggered by the optical detection of an analyte molecule at a defined position within the transport nanochannel.

The voltage steps can be triggered by the electrical detection of an analyte molecule using ionic current, tunneling current, or field effect transistor measurements at a defined position within the transport nanochannel.

The method can include electronically detecting a voltage change associated with passage of an analyte at a first portion of the fluid transport nanochannel before the intersection to initiate an automated cycle of applying and removing the bias to selectively inject, trap and transport a respective macromolecule in and through the fluid transport nanochannel for analysis It is noted that aspects of the invention described with respect to one embodiment, may be incorporated in a different embodiment although not specifically described relative thereto. That is, all embodiments and/or features of any embodiment can be combined in any way and/or combination. Applicant reserves the right to change any originally filed claim and/or file any new claim accordingly, including the right to be able to amend any originally filed claim to depend from and/or incorporate any feature of any other claim or claims although not originally claimed in that manner. These and other objects and/or aspects of the present invention are explained in detail in the specification set forth below. Further features, advantages and details of the present invention will be appreciated by those of ordinary skill in the art from a reading of the figures and the detailed description of the preferred embodiments that follow, such description being merely illustrative of the present invention.

BRIEF DESCRIPTION OF THE DRAWINGS

FIG. 3A illustrates the device with an exemplary ion distribution when no voltage is applied and FIG. 3B illustrates ion distribution when positive voltages are applied at the exit of the transport channel (V1) and at the two side channels (V2).

DESCRIPTION OF EMBODIMENTS OF THE INVENTION

Figure 1:
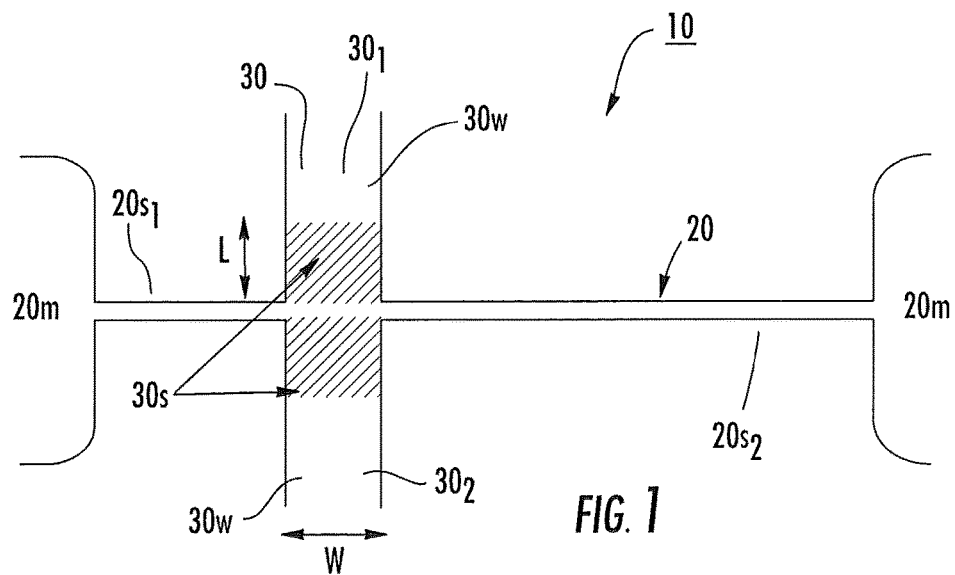
FIG. 1 is a schematic illustration of a device with wide, shallow nanofluidic channels positioned proximate a transport nanochannel according to embodiments of the present invention.

The present invention will now be described more fully hereinafter with reference to the accompanying figures, in which embodiments of the invention are shown. This invention may, however, be embodied in many different forms and should not be construed as limited to the embodiments set forth herein. Like numbers refer to like elements throughout. In the figures, certain layers, components or features may be exaggerated for clarity, and broken lines illustrate optional features or operations unless specified otherwise. In addition, the sequence of operations (or steps) is not limited to the order presented in the figures and/or claims unless specifically indicated otherwise. In the drawings, the thickness of lines, layers, features, components and/or regions may be exaggerated for clarity and broken lines illustrate optional features or operations, unless specified otherwise.

The terminology used herein is for the purpose of describing particular embodiments only and is not intended to be limiting of the invention. As used herein, the singular forms, "a", "an" and "the" are intended to include the plural forms as well, unless the context clearly indicates otherwise. It will be further understood that the terms "comprises," "comprising," "includes," and/or "including" when used in this specification, specify the presence of stated features, regions, steps, operations, elements, and/or components, but do not preclude the presence or addition of one or more other features, regions, steps, operations, elements, components, and/or groups thereof. As used herein, the term "and/or" includes any and all combinations of one or more of the associated listed items. As used herein, phrases such as "between X and Y" and "between about X and Y" should be interpreted to include X and Y. As used herein, phrases such as "between about X and Y" mean "between about X and about Y." As used herein, phrases such as "from about X to Y" mean "from about X to about Y."

It will be understood that when a feature, such as a layer, region or substrate, is referred to as being "on" another feature or element, it can be directly on the other feature or element or intervening features and/or elements may also be present. In contrast, when an element is referred to as being "directly on" another feature or element, there are no intervening elements present. It will also be understood that, when a feature or element is referred to as being "connected", "attached" or "coupled" to another feature or element, it can be directly connected, attached or coupled to the other element or intervening elements may be present. In contrast, when a feature or element is referred to as being "directly connected", "directly attached" or "directly coupled" to another element, there are no intervening elements present. Although described or shown with respect to one embodiment, the features so described or shown can apply to other embodiments.

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the present application and relevant art and should not be interpreted in an idealized or overly formal sense unless expressly so defined herein. Well-known functions or constructions may not be described in detail for brevity and/or clarity.

Spatially relative terms, such as "under", "below", "lower", "over", "upper" and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is inverted, elements described as "under" or "beneath" other elements or features would then be oriented "over" the other elements or features. Thus, the exemplary term "under" can encompass both an orientation of over and under. The device may be otherwise oriented (rotated 90 degrees or at other orientations) and the spatially relative descriptors used herein interpreted accordingly. Similarly, the terms "upwardly", "downwardly", "vertical", "horizontal" and the like are used herein for the purpose of explanation only unless specifically indicated otherwise.

It will be understood that, although the terms first, second, etc. may be used herein to describe various elements, components, regions, layers and/or sections, these elements, components, regions, layers and/or sections should not be limited by these terms. These terms are only used to distinguish one element, component, region, layer or section from another region, layer or section. Thus, a first element, component, region, layer or section discussed below could be termed a second element, component, region, layer or section without departing from the teachings of the present invention.

The term "nanochannel" refers to a channel or trench having a critical dimension that is at a nanometer scale. The nanochannel has sidewalls and a floor. The nanochannel can be formed into a solid substrate to have an open top surface and a closed bottom surface with the sidewalls extending therebetween. A cover may be used to seal or otherwise close the upper surface of the nanochannel(s). The term "primary dimension" refers to a width and/or depth dimension. The primary dimensions of a fluid transport nanochannel can be between about 1 nm to about 500 nm. The primary (also known as "critical") dimensions are both typically below about 100 nm, including between about 1-70 nm. In some embodiments, at least one primary dimension can be about 5 nm or less (on average or at a maxima).

The term "about" refers to parameters that can vary between +/−20% or less, such as +/−10%.

The term "transverse" nanochannel refers to a fluidic nanochannel that crosses a respective fluid transport nanochannel.

The term "fluid transport nanochannel" refers to a nanochannel therethrough which an analyte flows for analysis. The analyte can be any analyte of interest including, for example, single analyte molecules including synthetic and biological macromolecules, nanoparticles, small molecules, DNA, nucleic acids/polynucleic acids, peptides, proteins and the like. The transport through the nanochannel can be carried out using electrokinetics, concentration polarization and/or hydraulic pressure (forced pressure or pressure gradients).

The term "shallow" refers to nanochannel depths that have a lesser depth than a transport nanochannel and that are smaller than analyte macromolecules' hydrodynamic sizes. With respect to the depth of the transport nanochannel, the shallow nanochannel has a depth that is typically less by at least a factor of 2, such as by between 2-100×. Thus, for example, a shallow nanochannel segment can be 10 nm or less, typically between about 0.1 nm and 9 nm, while the transport nanochannel can have a depth (at least adjacent the shallow segment) that is 20 nm or more, such as between 20-100 nm.

The shallow channel segments $30s$ (FIGS. 1, 2A, 3 and 5) can be low ionic resistance channels that connect wide, deeper nanofluidic channels to the transport nanochannels.

The term "wide" means that the nanochannel has a width that is at least 2× that of a width of the transport nanochannel that it cooperates with to perform the analysis (e.g., provide a driving voltage), and more typically between 3×-100×, such as 3×, 4×, 5×, 6×, 7×, 8×, 9×, about 10×, about 20×, about 40×, about 50×, about 60×, about 70×, about 80×, about 90×, or about 100× the width of the adjacent cooperating transport nanochannel.

The term "circuit" refers to an entirely hardware embodiment or an embodiment combining software and hardware.

The term "low velocity" means that the macromolecule moves through the nanochannel at a velocity that is between about 0.1 μm/s and about 100 μm/s.

The term "significantly different field strengths" means that one side of the transport channel $20s_1$ can have a voltage/cm field strength that is 50×-1000×, typically 100×-200×, greater or smaller than a second segment of that same channel $20s_2$.

The term "capture" means that an analyte molecule present in a microchannel or reservoir accessing the entrance(s) to the transport nanochannel(s) 20 is successfully introduced to the nanochannel.

The term "threading" means the process by which the analyte molecule is initially introduced to the transport nanochannel 20, providing for the linearization of a macromolecule from the random coil conformation realized in the microchannel or reservoir.

The term "trap" means that an analyte molecule is immobilized at a specific location within the transport channel 20, usually at or near the intersection with the transverse nanofluidic elements 30, due to an electric field or concentration gradient or due to a physical impediment.

In some particular embodiments, the fluid transport nanochannels 20 (FIG. 1) can be defined as conduits having lengths substantially commensurate with, or exceeding, the analyte's contour length. If the nanochannel's width and depth are smaller than the radius of gyration of the macromolecule, then confinement of the molecule in the nanochannel necessarily results in molecular extension. The molecule's extended configuration will include a string of non-penetrating blobs (e.g., agglomerations) if the nanochannel width and depth are greater than the persistence length of the polymer (~50 nm for double-stranded DNA). Alternately, if the nanochannel critical dimensions are smaller than the persistence length, the molecule, unable to fold back on itself, can assume a reflecting rod conformation. In either case, the extension of a macromolecule along the length of a nanochannel facilitates single molecule characterizations. Specifically, the confinement of DNA in nanochannels has proven useful for sizing, mapping, separations, and epigenetic analysis.

Generally stated, devices and systems provided by embodiments of the invention allow a high level of control over the introduction of charged macromolecules (e.g., DNA, RNA, proteins, peptides, synthetic polymers) to nanofluidic channels. In this approach, an intersection of nanofluidic channels is used to provide control over the electric field strength in discrete segments of a transport nanochannel.

By way of simple illustration, one example of a device 10 is shown in FIG. 1. In this embodiment, the device 10 includes transverse nanofluidic elements 30 that interface to the transport nanochannel 20 through shallow nanochannels 30s. The transport nanochannel 20 has a segment $20s_1$ on one side of the cross channel and another segment $20s_2$ on the other side. As noted above, each side of the channel $30_1$, $30_2$ can have these shallow segments 30s with depths that are smaller than the analyte macromolecules' hydrodynamic sizes and the depth of the transport nanochannel. This ensures that the macromolecules will not migrate through the transverse channels 30 under appropriate operating conditions but will remain in the transport nanochannel 20. The shallow segments 30s can have a length of about 50 nm to about 10 μm or longer. The shallow segments 30s for each side $30_1$, $30_2$, of the respective nanochannel 30 can have the same depth and/or length or a different depth and/or length.

The shallow channel segments 30s can be low ionic resistance channels that connect to longer, wide, deeper nanofluidic segments 30w. Typically, the wider, deeper segments 30w reside between the shallow segments 30s and a reservoir or microfluidic channel 30m. The wider, deeper segments 30w can be 3 to 100 times the width and depth of the transport nanochannel 20.

Figure 2A:
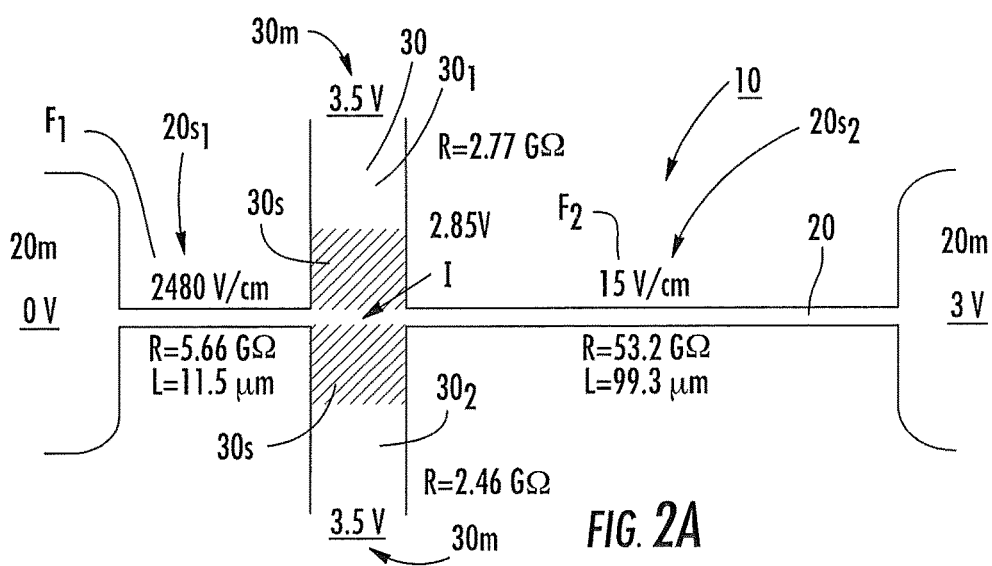
FIG. 2A is a schematic illustration of a device similar to FIG. 1 illustrating exemplary electric field strengths, ionic resistances (R) in segments and length (L) of the segments, of a transport nanochannel according to embodiments of the present invention.

FIG. 2A (not to scale) shows different electric field strengths in segments of a transport nanochannel 20, as established in an example device 10. The voltages applied at the four nanochannel outlets 30m, 20m in fluid communication with the respective nanochannels 30, 20 are underlined. The voltages applied to the transport channel microfluidic reservoir or outlets 20m are shown as 0V and 3V, respectively. In the devices 10 that include fluidic nanochannels 20, 30, the voltages can be applied using macroscopic electrodes inserted into respective fluidic reservoirs that access the corresponding nanochannels as is known to those of skill in the art.

The side channels 30 have 3.5V each applied to their outlets 30m. The measured ionic resistances, R, are indicated for channel segments $20s_1$, $20s_2$ and $30_1$, $30_2$. From these values, the voltage at the intersection "I" can be calculated. Finally, given the lengths, L, of the nanochannel segments $20s_1$, $20s_2$, the electric field strengths $F_1$, $F_2$ can be determined. In this example, transport in the left hand segment of the transport nanochannel $20s_1$ is 165 times faster than transport in the right hand segment $20s_2$.

The first segment $20s_1$ can be shorter than the second $20s_2$, typically having a length that is between 10-50% of the length of the longer segment, more typically a length that is between 10-20% that of the longer segment.

Figure 2B:
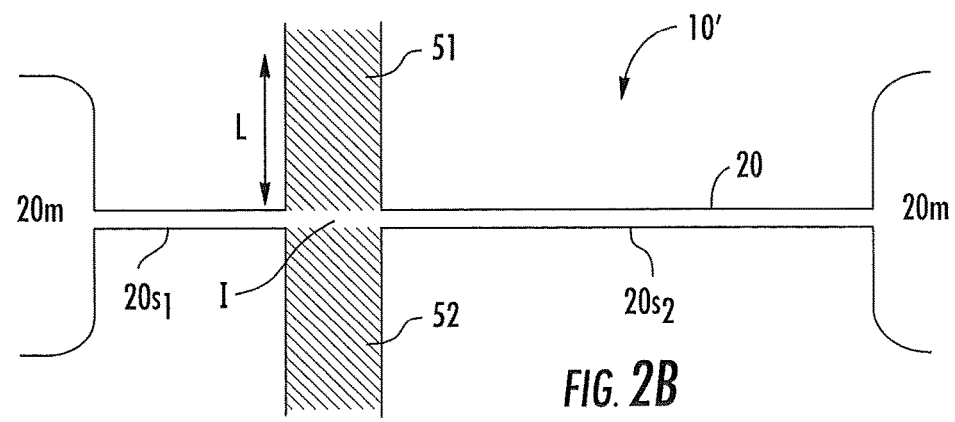
FIG. 2B is an alternate embodiment of a nanofluidic analysis device which includes integrated transverse electrodes positioned next to the transport nanochannel according to embodiments of the present invention.

FIG. 2B illustrates a differently configured device 10 having similar function but with the transverse nanochannels replaced by transverse electrodes 51, 52 that abut the transport channel 20. The electrodes 51, 52 can be integrated into the substrate of the device or attached to the substrate of the device adjacent the transport channel 20. The transverse electrodes can have a length L that is about 10 μM to about 5 mm or up to about 2 cm long and/or otherwise configured to provide suitable voltages, typically between about 1-20 V. Devices 10 that use integrated electrodes 51, 52 may exhibit limited lifetimes due to electrode fouling/degradation. This may be reduced or minimized by using electrode coatings or using appropriate anti-fouling or fouling resistant electrode material.

These devices 10 can provide fine control over analyte capture rates, as well as on the forces applied to macromolecules during capture, and their transport velocity within the nanochannel 20. This control over capture and transport dynamics can be achieved by device operation in different modes, the nature of which are determined by nanochannel dimensions and operating conditions. In one mode of operation, which can be described as the voltage divider mode, the resistance of each fluidic pathway is engineered by the choice of relative nanochannel widths, depths, and lengths. The field strength in each nanochannel is further controlled by the voltages applied at each nanochannel outlet.

FIGS. 2A and 2B shows an example of how this mode of operation can be used to capture molecules at high frequencies, given the high field strength in the portion of the transport nanochannel located to the left of the intersection I. Once the macromolecule migrates past the intersection, its velocity decreases significantly because it is driven by the weaker electric field in the portion of the transport nanochannel located to the right of the intersection in FIGS. 2A and 2B. The voltage divider mode of operation can also be achieved using integrated electrodes instead of the transverse fluidic elements (FIG. 2B). Such electrodes 51, 52 (comprising conductive materials such as metals, conductive polymers, conductive ceramics, etc.) serve to control the voltage at the electrode/nanochannel intersections I. Low velocity transport is useful for "on-the-fly" characterizations of macromolecules because it ensures that the molecules assume equilibrium conformations and that detection methods with limited temporal resolution can be used for analyses.

Figure 3A:
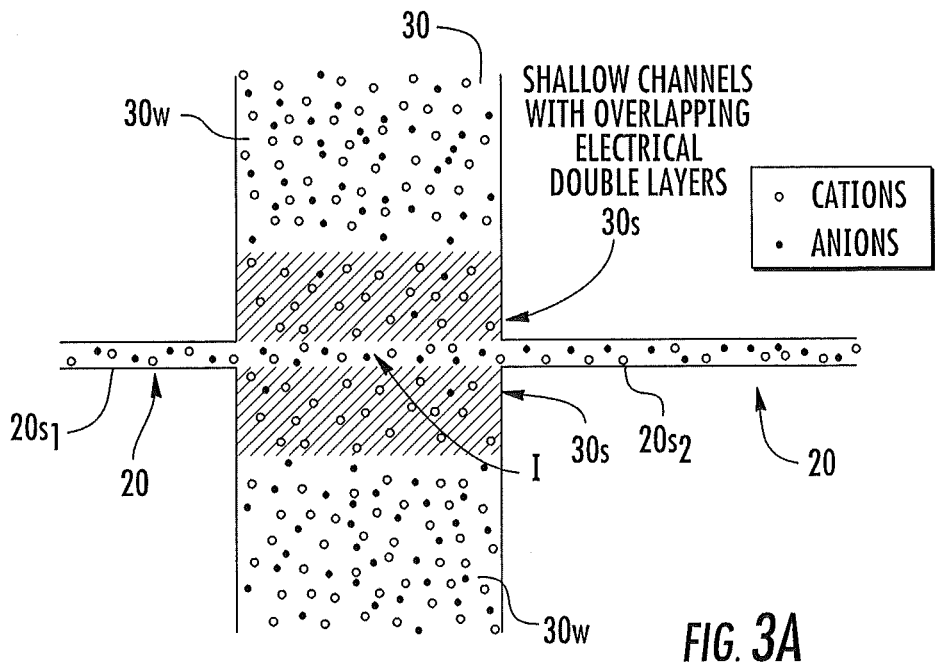
FIGS. 3A and 3B are schematic illustrations of a nanofluidic device with nanochannels configured for polyelectrolyte introduction into a transport nanochannel and subsequent trapping using concentration polarization [cations (the anions are shown with X markings to distinguish them from cations for black and white copies)].
Figure 3B:
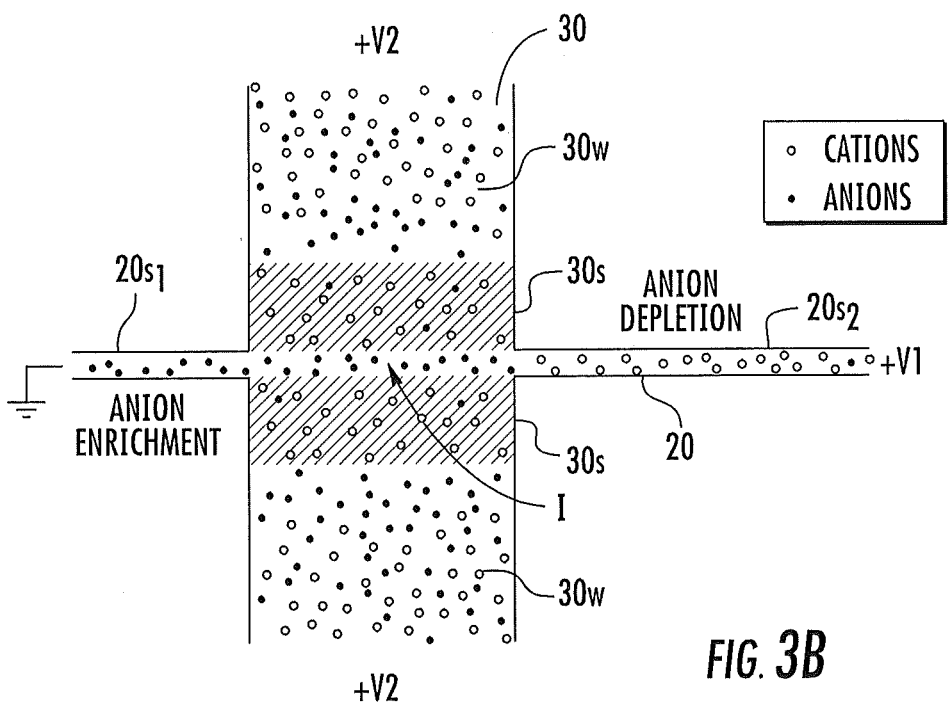

FIGS. 3A and 3B are schematic illustrations of a device 10 containing at least one nanochannel 20 designed for polyelectrolyte introduction into a nanochannel 20 and subsequent trapping using concentration polarization. Cations are orange and anions are illustrated in green (in the black and white version, with hatch marks). FIG. 3A shows ion distribution schematically when no voltages are applied to the device. FIG. 3B shows ion distribution when positive voltages are applied at the exit of the transport nanochannel (V1) and at the two side channels $30_1$, $30_2$, (V2), showing anion enrichment and depletion.

In some exemplary mode of operation, nanochannel dimensions and buffer conditions are selected such that concentration polarization occurs at the nanochannel intersection I. For nanochannels with negatively charged surfaces (e.g., nanochannels fabricated in quartz substrates and buffer pH above $pK_a$ of surface silanol groups), the concentration of anions can be enhanced at the intersection I while the concentration of cations is depleted. Realizing this condition means that the transverse nanochannels 30 be sufficiently shallow and/or the ionic strength of the buffer sufficiently low to achieve an overlap of the electrical double layers within these nanochannels. The concentration polarization is illustrated schematically in FIGS. 3A and 3B. Because of concentration polarization in this configuration, polyanionic macromolecules such as DNA and RNA can be driven into the transport nanochannel with a high field strength and are subsequently trapped at the nanochannel intersection. Whether molecules are trapped at the intersection I or dramatically slowed after passing through the intersection, the change in dynamics provides sufficient time for the voltages to be adjusted in order to control precisely macromolecule transport through the nanochannel with arbitrary velocity and directionality. An example of a configuration showing such operation is illustrated in FIGS. 4A-C.

As shown in FIGS. 3A and 3B, the shallow channel segments 30s can have an overlapping electrical double layer. As is known by those of skill in the art, when a charged surface (silica surfaces are negatively charged at pH>3) is in contact with a solution it will attract ions of an opposite charge (i.e., glass attracts positive ions). The presence of these ions shields the surface charge. Close to a charged surface, a layer of oppositely charged ions can be present that has a concentration that is locally greater than in the bulk solution. This is called the electrical double layer (EDL) There is a characteristic length scale associated with the EDL called the Debye length. If an ion in solution is farther from the surface than this Debye length, then the surface charge is fully shielded. If it is closer to the surface than the Debye length, then the ion experiences an electrostatic interaction with the surface (i.e., it will be attracted to the surface if it is of opposite charge or repelled if it is of the same charge). The Debye length is a function of solution ionic strength and, for low ionic strength solutions in shallow nanochannels, a condition can occur where the double layers of opposed surfaces overlap. Due to charge repulsion, there is an inhibitory effect reducing the concentration of ions in the nanochannels if they have the same charge polarity as the nanochannel walls. Conversely, due to charge attraction, there is an enhancement effect increasing the concentration of ions in the nanochannels if they have the opposite charge polarity of the nanochannel walls. When a voltage is applied across a shallow transverse nanochannel 30 which intersects the transport nanochannel 20, "concentration polarization" occurs due to the different transport rates of oppositely charged ions through the shallow nanochannel. Devices having negatively charged channel walls can create zones where negatively charged ions (like DNA) can be trapped and zones where positively charged ions are excluded. Devices having positively charged channel walls create zones where positively charged ions (like some proteins) can be trapped and zones where negatively charged ions are excluded.

Figure 4A:
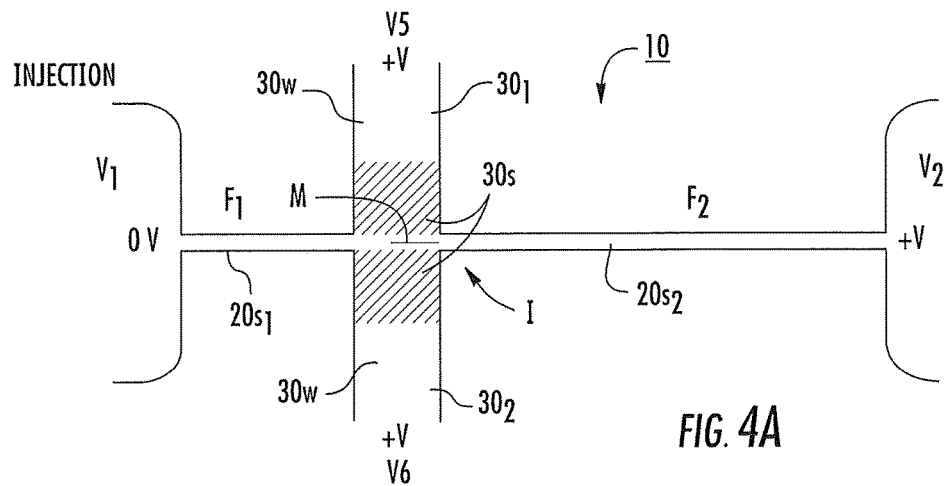
FIGS. 4A-4C are schematic illustrations of an exemplary device with three phases of operation (injection (4A), equilibrium (4B) and transport (4C)) according to embodiments of the present invention.
Figure 4B:
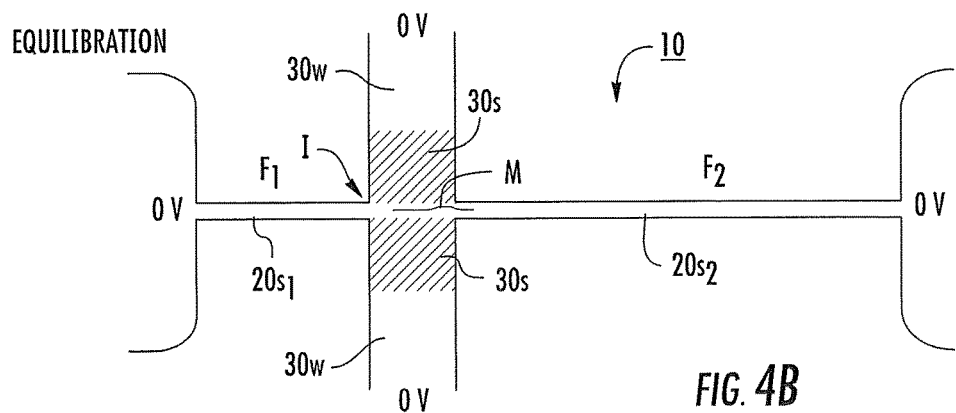
Figure 4C:
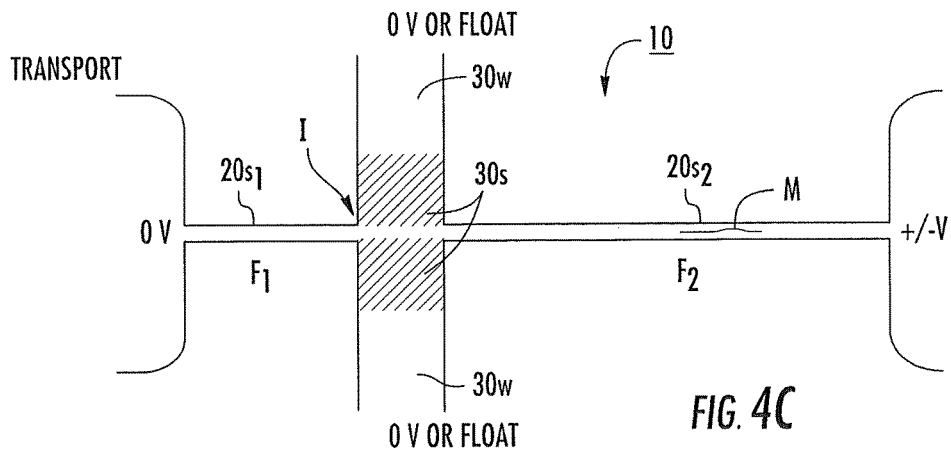

FIGS. 4A-C show three phases of operation for a device having an intersection I of appropriately sized nanochannels 30. Applying a positive bias to the nanochannel reservoirs not containing the polyanionic macromolecule ("M") results in analyte injection and trapping (FIG. 4A). Removing all biases causes the molecule M to relax to an equilibrium conformation (FIG. 4B). Applying a bias solely across the transport nanochannel controls translocation through the nanochannel (FIG. 4C). This transport step can achieved using two different modes of operation. In the first mode, a voltage is applied across the transport nanochannel (V1, V2) while the electrodes in the transverse shallow nanochannels $30_1$, $30_2$ are floated (i.e., no voltage is applied nor are the electrodes grounded). In the second mode, a voltage is applied across the transport nanochannel 20 (V1, V2) while the electrodes in the transverse shallow nanochannels $30_1$, $30_2$ (V3, V4) are grounded.

Nanochannels are well suited for a number of applications including single molecule detection and identification, confinement and manipulation of biopolymers, biological assays, restriction mapping of polynucleotides, DNA sizing, physical methods of genomic sequencing, and fundamental studies of the physics of confinement.

It is expected that the successful implementation of many of these applications will require the careful control of molecular dynamics within the nanochannels, including the velocity of molecular transport and the frequency with which analyte molecules are driven through the nanochannels. The transport of a macromolecule from macroscopic and microscopic reservoirs through nanofluidic conduits that are smaller than the molecule's radius of gyration requires the application of a driving force (e.g., hydrodynamic, electrostatic, gravitational) to overcome an energy barrier. This barrier is primarily entropic in nature and derives from the reduction in the molecule's conformational degrees of freedom in moving from free solution to the confining nanochannel. Additionally, the probability of a successful transport event is proportional to the likelihood that the molecule collides with the entrance of the nanofluidic conduit in a conformation favorable to threading. The practical implication of these fundamental conditions is that molecular transport does not occur until a finite threshold driving force is applied. The magnitude of the requisite force may be considerable, resulting in transport of the analyte through the nanochannel at high velocity. The energy barrier precludes driving transport at lower velocity, which may be desirable for many applications. Additionally, the application of large forces to large macromolecules may induce fragmentation during the capture process. Both of these limitations can be overcome by using nanofluidic devices such as those described here. The overall force pulling on macromolecules during their introduction into a transport nanochannel is a function of the field strength in the nanochannel and the number of charged monomers contained within the high-field segment of the transport nanochannel. Therefore, this force can be adjusted by controlling the applied voltages or the length of the high-field segment of the nanochannel.

This may be especially important for the nanochannel confinement of extremely long macromolecules such as genomic DNA. Consider, for example, the introduction of human chromosomal DNA to a centimeter long, 100-nm diameter nanochannel. The median length for human chromosomal DNA is ~130 Mbp (mega base pairs). With a radius of gyration of ~80 μm, DNA of this length has considerable conformational entropy. An estimated threshold field strength of ~10 kV/cm would be required to overcome the entropic barrier and pull the DNA into the transport nanochannel. This can be achieved by applying 10 kV across a 1-cm long nanochannel or by applying 10-20 V at the outlets of an injection device such as those described here. If the high-field segment of the transport nanochannel is 1 μm long, then the total force applied to the DNA molecule during threading is $10^5$ times smaller in the injection device (~5 kbp are contained in the high-field region). This greatly reduces the probability of DNA fragmentation.

Exemplary Device Fabrication

Figure 5A:
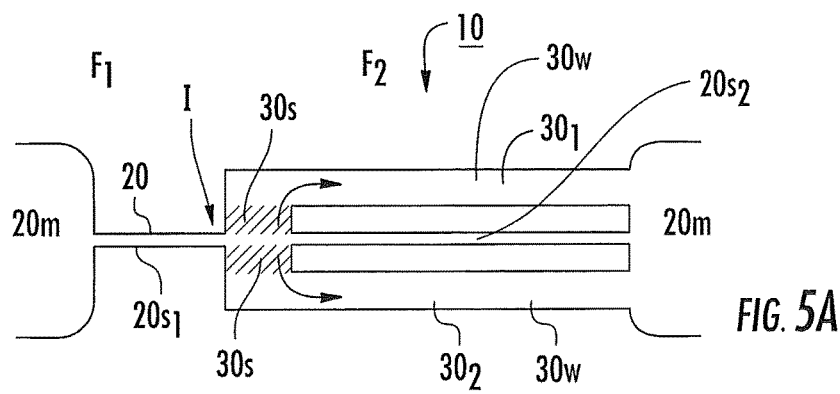
FIG. 5A is a schematic illustration of a device with macromolecule transport with a different shallow channel geometry that can be controlled by applying a single voltage across the nanochannel network of the device according to embodiments of the present invention.
Figure 5B:
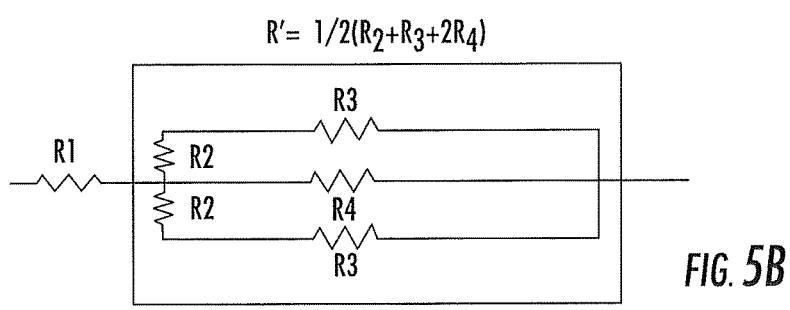
FIG. 5B is a circuit diagram of an equivalent electric circuit indicating ionic resistances through the nanochannels according to embodiments of the present invention.
Figure 5C:
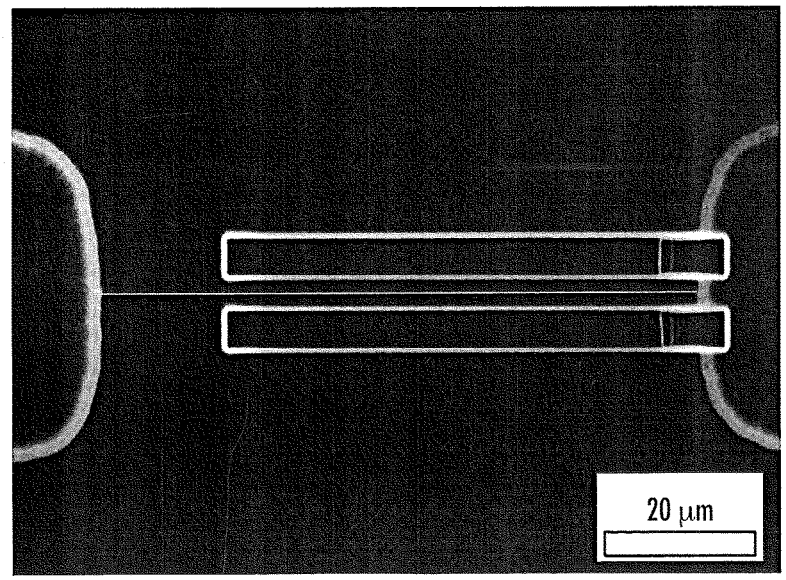
FIG. 5C is a top-down SEM image of the devices shown with respect to FIGS. 5A and 5B.
Figure 5D:
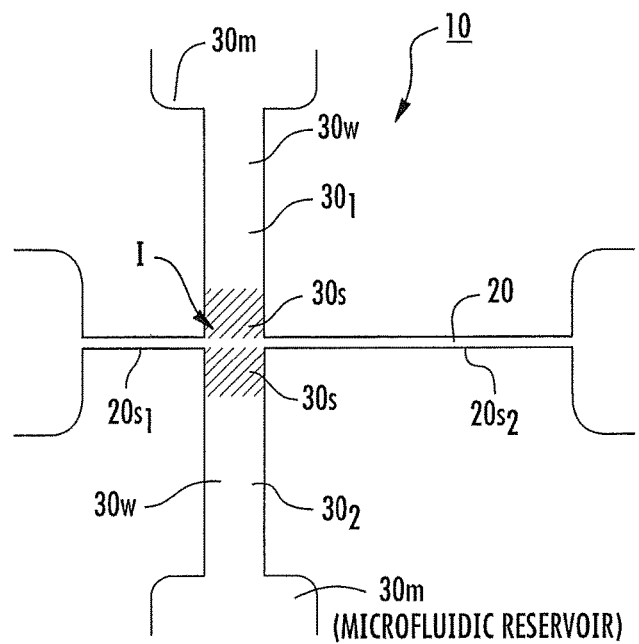
FIG. 5D is a schematic illustration of a device where macromolecule transport is controlled by applying voltages to each of the nanochannels independently according to embodiments of the present invention.

Two device configurations are shown in FIGS. 5A and 5D. A unifying characteristic for these configurations is the various nanochannel 20, 30 dimensions. The nanochannels' lateral dimensions through which analyte transport is driven 20 can be on the order of 20-100 nm in these examples and have an aspect ratio (width:depth) close to 1. The shallow channels 30s intersecting the transport nanochannel 20 can have a critical dimension (depth) that is between about 1 to 10 nm. As discussed above, two considerations inform this element of device design. First, the smaller dimension, relative to the transport nanochannel dimensions, prevents the unwanted transport of analyte macromolecules through these conduits. Second, these dimensions are commensurate with the characteristic Debye length of the electrical double layer in low ionic strength buffers, meaning that concentration polarization can be induced in standard electrophoresis buffers such as 1×TBE (89 mM Tris; 89 mM borate; 2 mM ethylenediamenetetraacetic acid, EDTA). If concentration polarization is not desired, then deeper transverse nanochannels 30 and higher ionic strength buffers are used.

The device 10 shown in FIG. 5A can manipulate analyte molecules through control of a single applied voltage V, with the field strengths through the various nanochannels determined by their relative resistances (FIG. 5B). The channel dimensions are chosen to realize a significant voltage drop between the sections of the transport nanochannel that are pre- and post-intersection. A second, more flexible device design is shown in FIG. 5D (which is similar to that shown and discussed above with respect to FIGS. 1, 2A). Here the same elements are present but the intersecting nanochannels $30_1$, $30_2$ are individually addressable, enabling precise control of macromolecular transport.

FIG. 5A illustrates the nanochannel 20 merges into the nanofluidic channels 30 at an intersection I forming the two segments (short $20s_1$ and long $20s_2$). In this embodiment, the two segments $30_1$, $30_2$ are substantially parallel and extend along a length of the long segment $20s_2$. In this embodiment, macromolecule transport can be controlled by applying a single voltage across the nanochannel network.

The shallow channel segments $30s$ can be low ionic resistance channels that connect the longer, wide, deeper nanofluidic segments $30w$ of nanochannels $30_1$, $30_2$, which are the same or substantially the same length as the segment $20s_2$, to the transport nanochannel 20 at the intersection I. The wider, deeper nanochannels $30w$ are configured so that most of the voltage is dropped over segment $20s_1$, resulting in a much lower field strength in segment $20s_2$ (i.e., F2<<F1 for low velocity or no flow (trapping)).

FIG. 5B is an equivalent circuit diagram indicating the ionic resistances through the nanochannels of FIG. 5A. FIG. 5C is a top-down SEM image of the device shown in FIG. 5A.

Figure 5E:
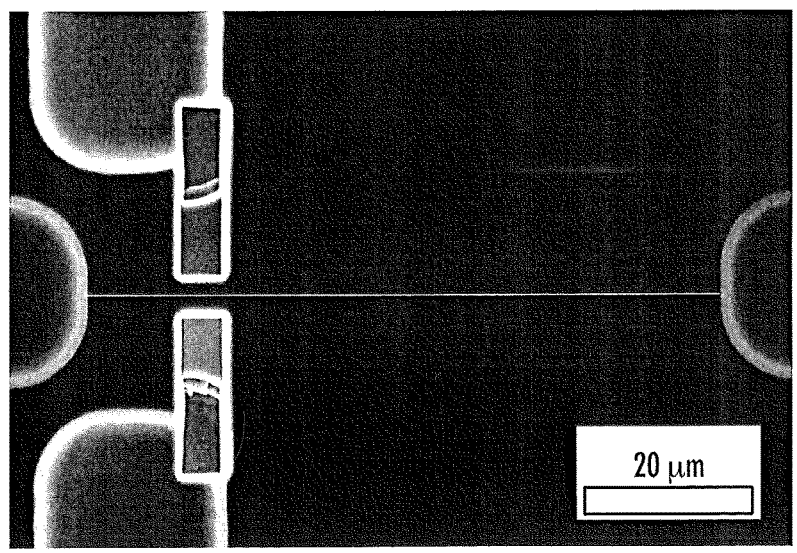
FIG. 5E is an SEM image of a four-reservoir device associated with the configuration of FIG. 5D.

FIG. 5E is a SEM image of a four-reservoir device.

The fluidic nanochannels can be fabricated using a variety of techniques including focused ion beam (FIB) milling, electron beam lithography, nanoimprint lithography, photolithography, templating or molding strategies. These methods are applicable to a variety of substrate materials, enabling device fabrication in glass (silica), quartz, silicon, ceramics, metals, plastics, etc.

In the case of the devices 10 described here as examples of the invention, a combination of electron beam lithography and FIB milling are used to pattern the nanofluidic elements. First, microfluidic channels are prepared using standard photolithographic and etching techniques. These microchannels are accessed by powder-blasted vias. The shallow transverse nanochannels were then defined by patterning the features using electron beam lithography. The features were etched 1-10 nm into the quartz using a wet chemical etch. Alternatively, these features could have been patterned using a variety of methods listed above. The transport nanochannel was fabricated using FIB milling on a Helios NanoLab DualBeam Instrument (FEI Company) with a $Ga^+$ ion source operated at 30 kV. Next, the shallow channel is interfaced to the microfluidic channels by FIB milling large (5 µm wide×2 µm deep), low resistance channels. FIGS. 5C and 5E show SEM images of the devices after these elements have been patterned. Finally, any film layers on the substrate surface required in the various patterning steps are removed and the fluidic network enclosed by sealing the device with a coverslip using one of several possible methods such as fusion bonding, anodic bonding, or adhesive bonding.

Confirmation of Concentration Polarization in Injection/Trapping Device

Figure 6A:
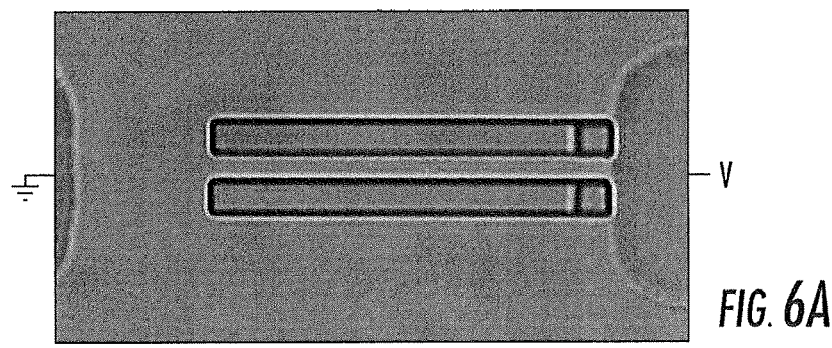
FIG. 6A is a bright field optical microscopy image of an injection/trapping device according to embodiments of the present invention.
Figure 6B:
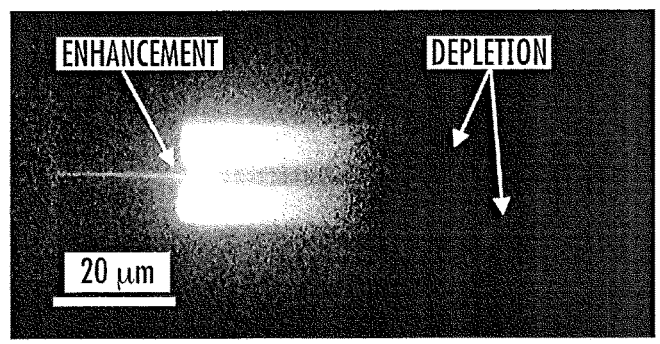
FIG. 6B is a fluorescence microscopy image showing concentration enhancement and depletion of fluorescein dye in a 0.5×TBE buffer when 4V is applied across the nanochannel network according to embodiments of the present invention.

To confirm that concentration polarization was occurring during the operation of devices with intersecting nanochannels, the concentration profile of an anionic fluorescent dye, fluorescein, was measured during operation of the device type shown in FIG. 5A, A 10 µM solution of fluorescein was prepared in 0.5×TBE buffer (89 mM Tris; 89 mM borate; 2 mM ethylenediamenetetraacetic acid, EDTA). This solution was introduced to the microfluidic channels accessing both sides of the nanofluidic network. The device was mounted on an inverted microscope and fluorescence images were recorded of the nanofluidic channels. A voltage was applied across the nanochannels as indicated in FIG. 6A. Images were collected when no voltage was applied and after applying a voltage across the nanochannels and allowing the dye to respond. By subtracting the zero-bias fluorescence image from one collected when a voltage was applied, the regions of fluorescein concentration enhancement and depletion become apparent. FIG. 6B shows one of these difference images, which clearly indicates the presence of concentration polarization.

FIG. 6A shows a bright field optical microscopy image of an injection/trapping device. FIG. 6B shows a fluorescence microscopy image showing the concentration enhancement and depletion of fluorescein dye in 0.5×TBE buffer when 4 V is applied across the nanochannel network according to embodiments of the invention.

Control of DNA Transport in Injection/Trapping Devices

Figure 7:
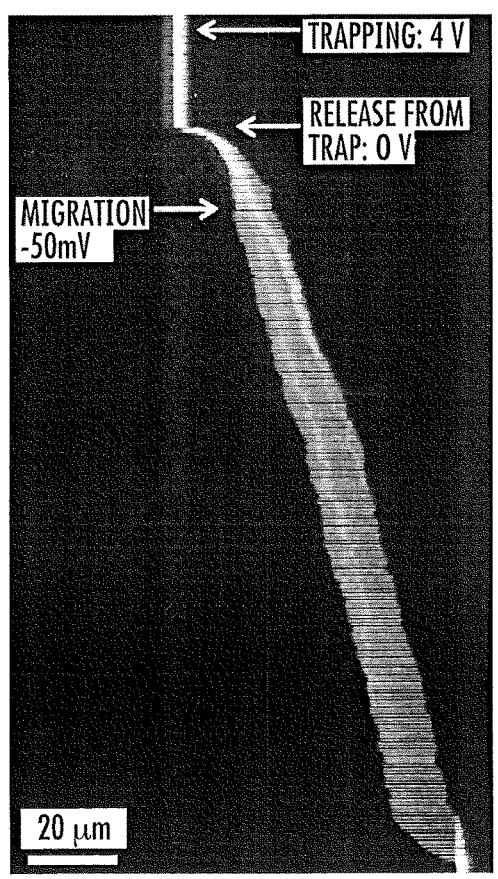
FIG. 7 is an image of a series of frames showing trapping and subsequent transport of λ-DNA through a device similar to that shown in FIG. 5A according to embodiments of the present invention. The frame rate is 200 ms/frame. The arrows indicate when the noted voltages were applied.

In a device with a single voltage control such as that shown in FIG. 5A, transport can be controlled by manipulating the concentration polarization, as shown in FIG. 7. Injection of DNA occurs by applying a sufficiently large positive voltage. The DNA threads into the transport nanochannel and quickly migrates to the nanochannel intersection where it is trapped.

FIG. 7 shows a series of frames showing the trapping and subsequent transport of λ-DNA through a device similar to that shown in FIG. 5A. Concentration polarization is present as evidenced by the strong trapping of DNA. The frame rate is 200 ms/frame. The arrows indicate when the noted voltages were applied.

As is apparent in FIG. 7, the trapping force results in compression of the molecule. Upon removing the applied bias, two forces act upon the molecule, resulting in a transient response. The first is the relaxation of the compressive forces imposed on the molecule during trapping. The second is the equilibration of ionic concentration profiles. This latter contribution generally ensures that the DNA molecule drifts into the transport nanochannel on the side opposite of the injection segment of the nanochannel. At this point, applying a small negative voltage results in DNA transport towards the negative electrode. This transport is counter to the direction expected for the electrophoresis of negatively charged DNA. It originates from DNA transport along a front of anion depletion from the nanochannel intersection.

Increased control of electrokinetically-driven macromolecular transport can also be realized in a device with a single voltage control such as that shown in FIG. 5A in the absence of concentration polarization. This condition can occur when the ionic strength of the electrolyte solution is high and/or the intersecting nanochannels are relatively deep. These conditions preclude or minimize electrical double-layer overlap and result in weak or negligible trapping. Under this scenario, there is still a considerable difference in electric field strength in the injection $20s_1$ and transport $20s_2$ segments of the transport nanochannel 20 due to the resistances in the nanochannel network (FIG. 5B).

Figure 8:
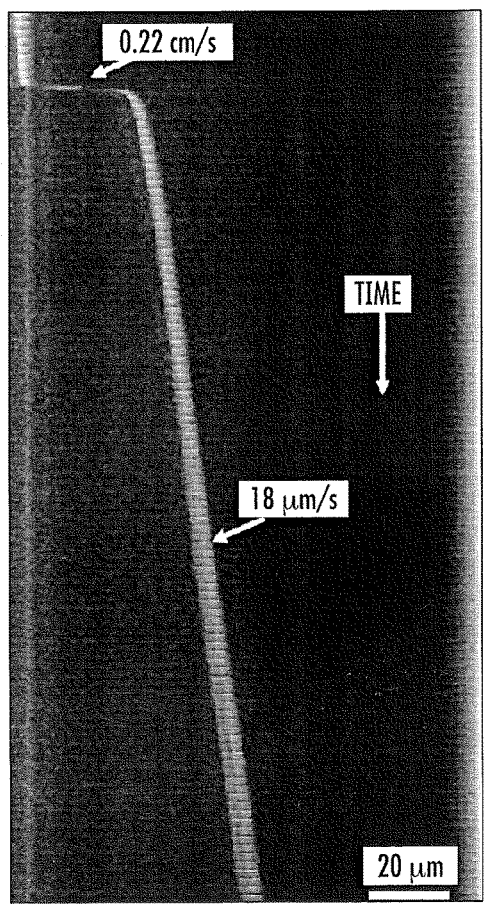
FIG. 8 is an image of a series of frames showing transport of λ-DNA through a device similar to that shown in FIG. 5A according to embodiments of the present invention. The frame rate is 4 ms/frame. A bias of 4V was applied across the fluidic network. The experiment was performed using a higher ionic strength buffer (10×TBE) to reduce DNA trapping. The arrows indicate velocity over time.

Consequently, DNA molecules can be injected at high field strengths while their velocity drops significantly upon passing through the nanochannel intersection and into the transport segment of the transport nanochannel. The relative strengths of the electric fields can be controlled by varying the channel dimensions in the device and the absolute values controlled by the magnitude of the voltage applied across the nanofluidic network. Fluorescence images recording a translocation controlled in this mode of operation are shown in FIG. 8. The applied voltage is held constant versus time during the operation of this device.

FIG. 8 illustrates a series of frames showing the transport of λ-DNA through a device similar to that shown in FIG. 5A. A bias of 4V was applied across the nanofluidic network. The experiment was performed using a higher ionic strength buffer (10×TBE) to reduce DNA trapping. The frame rate was 4 ms/frame.

The device type shown in FIG. 5D provides additional control over DNA transport. Since the two side nanochannels are individually addressable, the strength of the DNA trapping force can be tuned from weak to strong. After trapping, the voltages across the side nanochannels can be removed and the device acts as a single nanochannel in which transport is determined by electroosmotic or electrophoretic forces. These forces have magnitudes that are positionally invariant, meaning that application of a constant voltage will result in a constant transport velocity. Consequently, this configuration provides greater control than a device having a single voltage control in which transport is dependent upon the evolution of concentration gradients. This control is illustrated in FIG. 9, which shows that transport of a single DNA molecule can be turned off and on.

Figure 9:
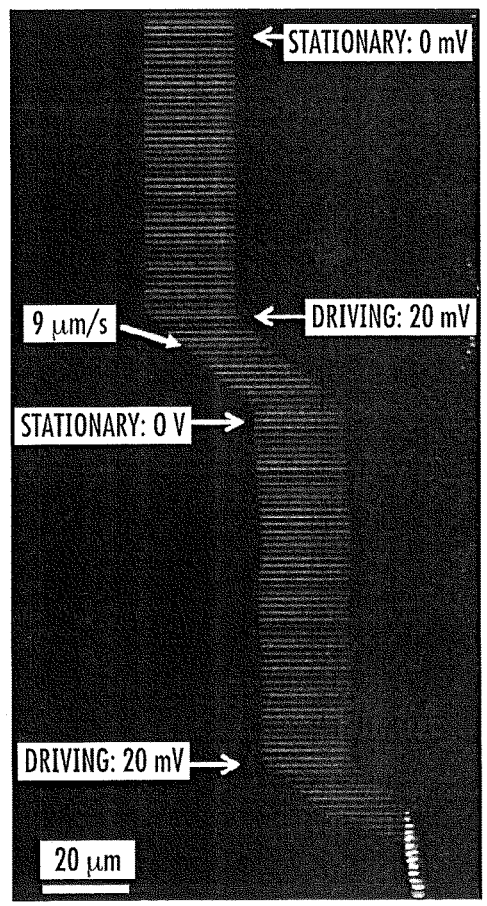
FIG. 9 is an image of a series of frames showing control over transport of λ-DNA through a device similar to that shown in FIG. 5D according to embodiments of the present invention. The frame rate is 200 ms/frame. DNA is held stationary or transported at low velocities through a 20 nm by 20 nm (width by depth) transport nanochannel. The arrows indicate when/where the noted voltages were applied.

FIG. 9 is a series of frames showing the control over transport enabled by a device configured similarly to the device shown in FIG. 5D. DNA is held stationary or transported at low velocities through a 20 nm×20 nm (width× depth) transport nanochannel. The frame rate is 200 ms/frame.

Embodiments of the invention provide active devices that generate large injection electric fields that can initiate a high frequency of transport events while simultaneously allowing fine control of analyte transport once the macromolecules are confined in the transport nanochannel. This is believed to be a capability unique to the class of devices described here. Concentration polarization has been used in microfluidic devices as a method of analyte preconcentration but has not been reported for use in single-molecule studies or devices as described herein. Nanofluidic devices having peripheral components similar to the shallow nanochannels used here have proven useful in the loading of nanofluidic channels with macromolecules using pressure-driven flow. Electrical forces may be more easily balanced and controlled than pressures through nanofluidic networks.

The potential uses of the devices, methods and systems provided by embodiments of the invention are broad in scope. Because of the increased control over transport-driving electric fields and trapping dynamics, macromolecule transport through nanochannels at lower velocity can be achieved. This is expected to allow more precise optical and electrical measurements on single confined molecules. One example is the sequencing of DNA molecules in a nanochannel interfaced to opposed tunneling probes in which base calling is achieved by measuring the unique tunneling currents through the individual nucleotides. A level of control is demonstrated that would allow, for example, transport in either direction and at various velocities, multiple passes of a single molecule, and ratcheted base-by-base movement. The described devices are also expected to be valuable for the introduction of long, intact macromolecules to nanofluidic channels. This ability would enable end-to-end characterizations of an entire chromosome's worth of DNA, for example.

Figure 10A:
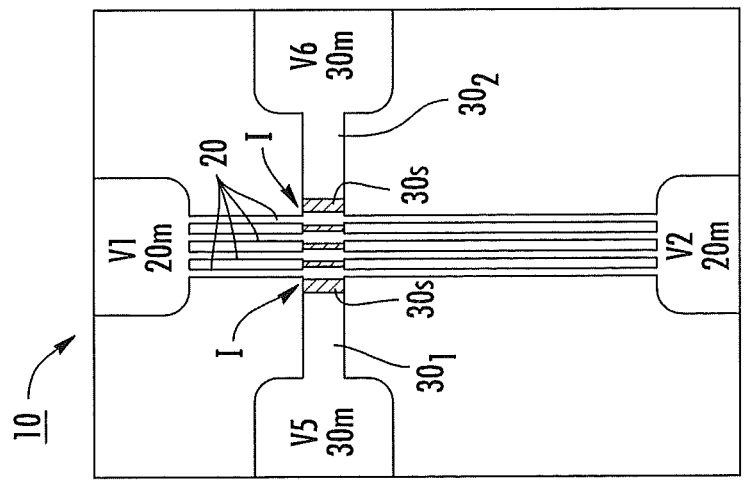
FIGS. 10A-10C are top schematic views of alternate nanofluidic channel configurations for applying voltage and/or concentration gradients for controlling trapping, capture and transport using a respective fluidic analysis device according to embodiments of the present invention.
Figure 10B:
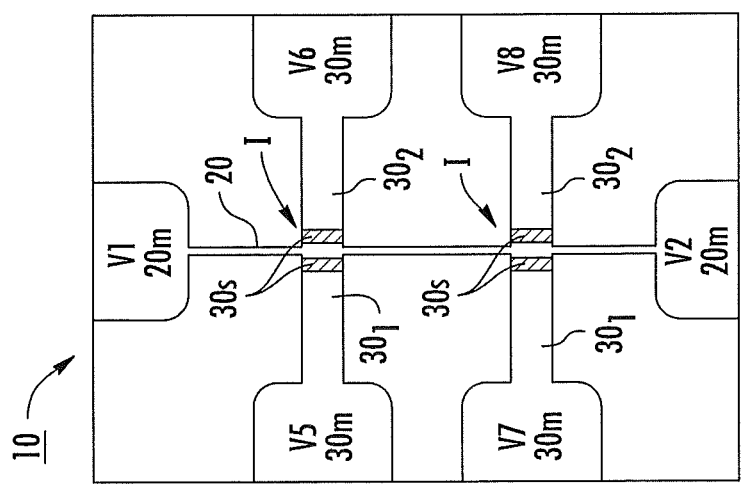
Figure 10C:
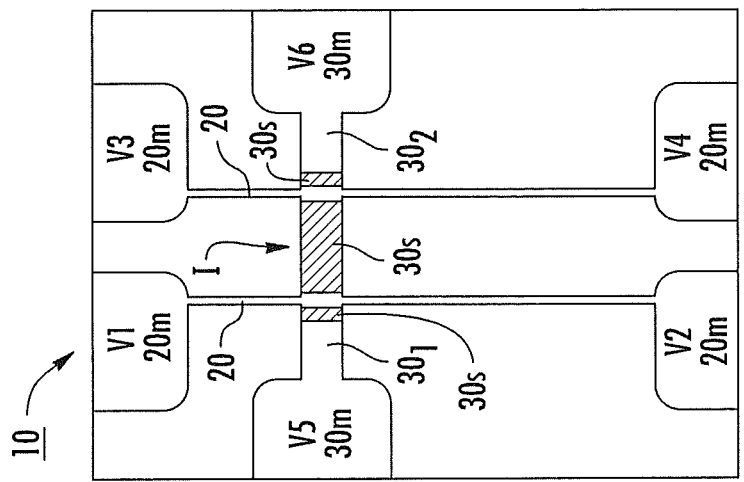

FIGS. 10A-10C illustrate alternate geometries of a fluidic analysis device 10 having one or more intersections with one or more cross-channels 30 configured to selectively apply the electrical bias V1, V2, V3, V4 at the end portion of the transport channel(s) 20 and V5, V6, V7, V8 at the end portion of the transverse nanochannel(s) 30. The white channels indicate normal channel depth/size, the striped pattern indicates shallow channel segments 30s.

Figure 11A:
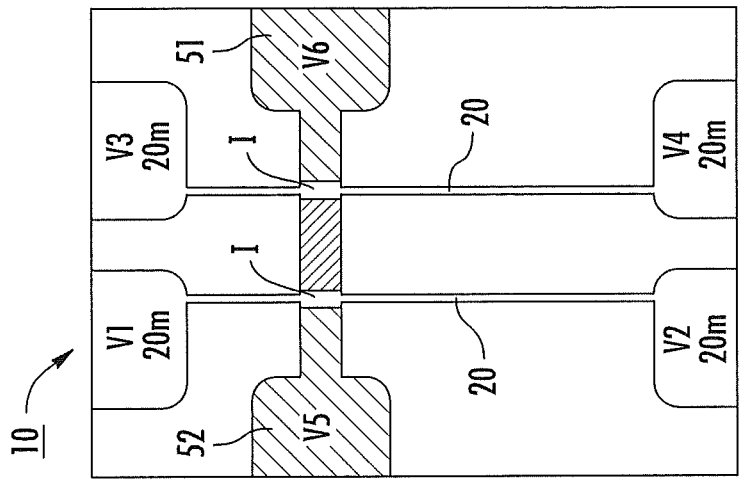
FIGS. 11A-11C are top schematic views of alternate exemplary configurations of transverse electrodes for applying voltage controlling trapping, capture and transport in a respective fluidic device according to embodiments of the present invention.
Figure 11B:
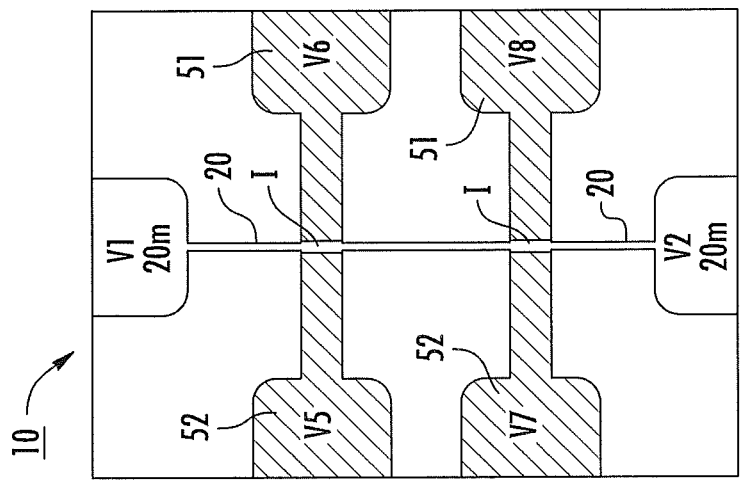
Figure 11C:
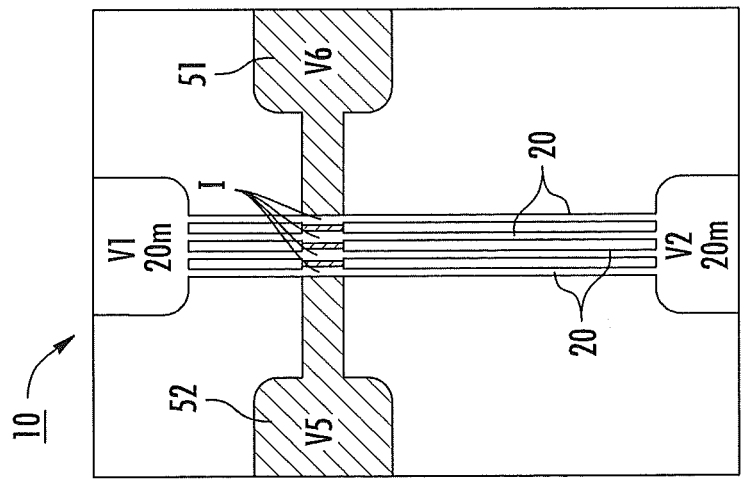

FIGS. 11A-11C illustrate alternate geometries of a fluidic analysis device with intersections of one or more sets of transverse electrodes 51, 52 to selectively apply the electrical bias V1, V2, V3, V4 at the end portion of the transport channel(s) 20 and V5, V6, V7, V8 at the transverse electrodes 51, 52.

Combinations of channels 30 and transverse electrodes 51, 52 with one or more transport channels 20 can be used on a fluidic device 10, such as a fluidic analysis chip (not shown).

Nanofunnels may also be used with one or more of the fluid channels as described in co-pending PCT/US2013/025078, the contents of which are hereby incorporated by reference as if recited in full herein.

Figure 12:
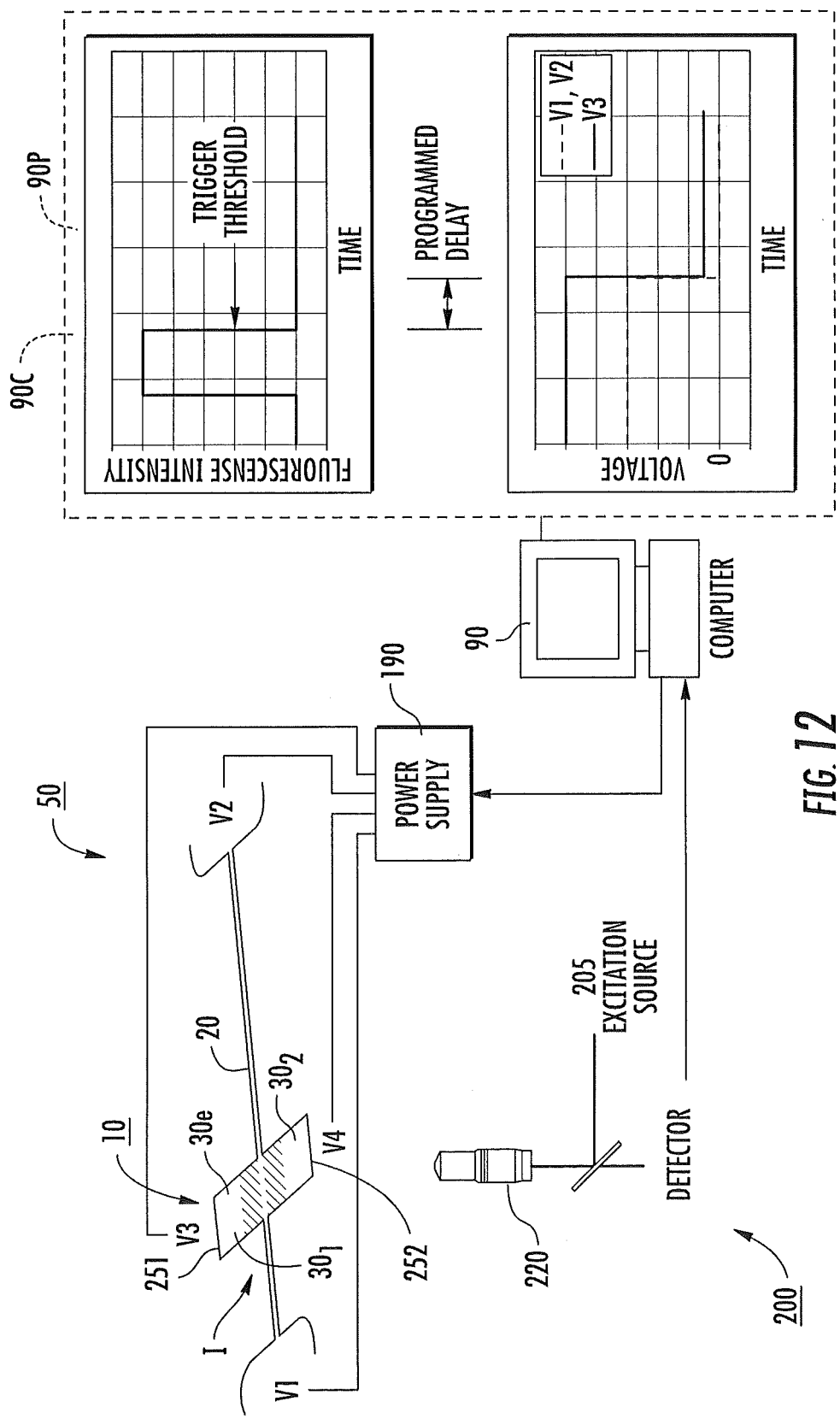
FIG. 12 is a circuit diagram of an exemplary circuit for operating a fluidic analysis device according to embodiments of the present invention.
Figure 13:
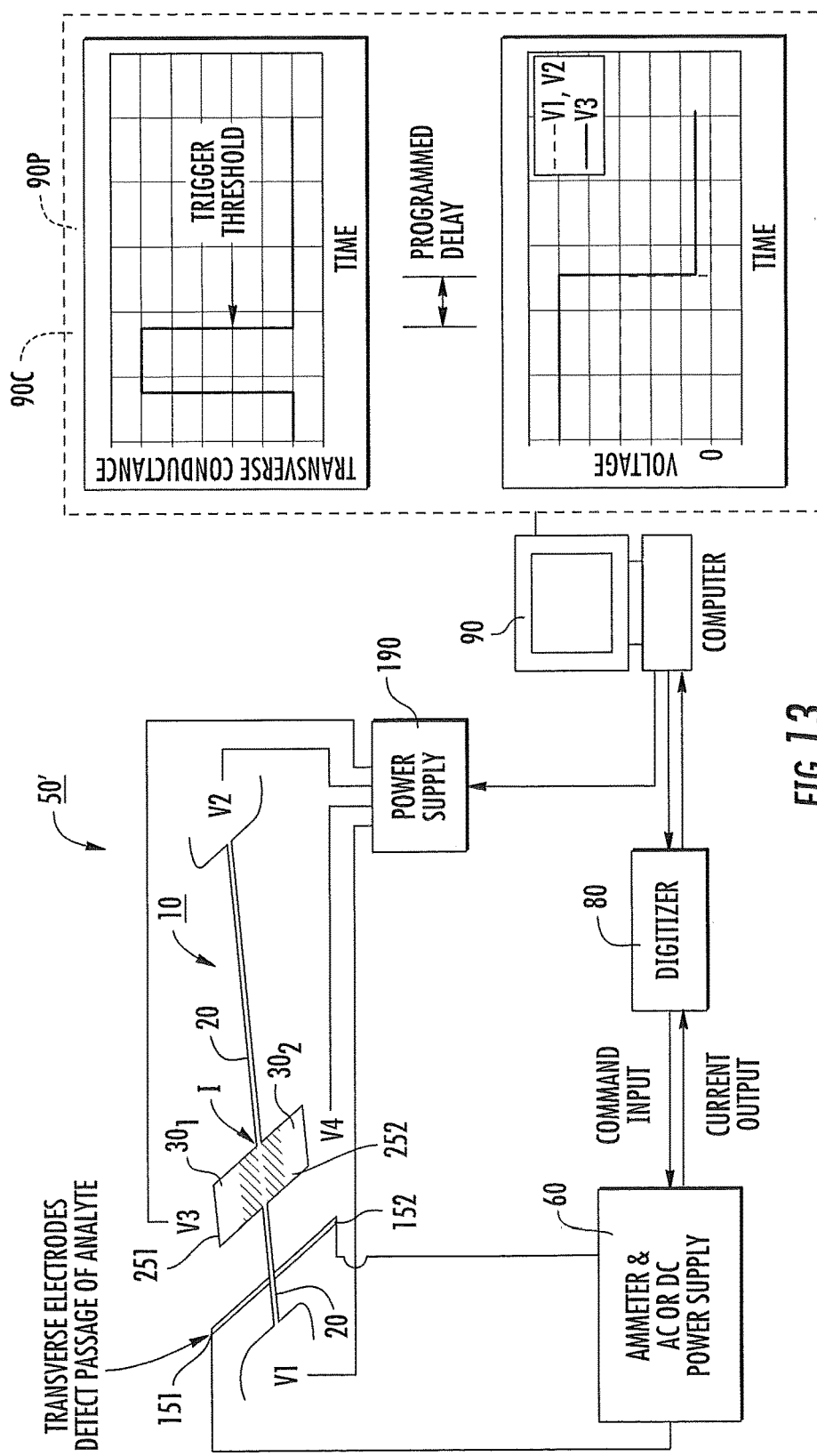
FIG. 13 is a circuit diagram of another exemplary circuit for operating a fluidic analysis device according to embodiments of the present invention.

FIGS. 12 and 13 illustrate exemplary circuits 50, which can include a power source 190 that can electrically apply an electrical bias, e.g., voltage, to the channel segments 20, 30 or the transverse electrodes 51, 52. One or both end portions of transport channel 20 and/or fluid cross channels 30 can merge into a reservoir that is configured to hold a flowable substance such as a fluid (electrolyte). The reservoir fluid can comprise an electrolyte solution, e.g., a high ionic strength electrolyte solution. The reservoir and channel 30 can comprise the same fluid as the transport channel 20, e.g., the same concentration of electrolyte solution or different concentrations of electrolyte solutions. Examples of suitable solutions include, but are not limited to, potassium chloride solutions in concentrations from about 35 mM to about 1 M. Alternatively, or additionally, a higher (or lower) ionic strength flowable material, liquid or solution can be used in the channel 30, relative to the solution in the transport channel 20. Other fluid materials that can be used for a respective channel 30 include amphiphilic electrolytes in organic solvents, electrolyte solutions in gels formed in the sensing channels, conducting polymers, ionic liquids, low melting temperature metals and alloys (e.g., "liquid metals").

Combinations of different flowable materials may also be used. In some embodiments where a transport channel 20 is intersected by more than one channel 30, each channel 30 may include a different flowable material or the same flowable material. In some embodiments, a respective channel 30 has the same electrolyte solution as another channel 30, at the same concentration or at different concentrations. In some embodiments, the fluid material can be converted to a solid or semi-solid material after introduction to the channels 30. For example, gels can be cross-linked, polymers can be polymerized, and metals can be solidified by lowering the device operating temperature below the metal's melting point. In other embodiments, embedded electrodes can be grown adjacent the transport channels for transverse electrodes 51, 52, using plating or growth methods (e.g., electroplating or electroless plating of metals) known to one of ordinary skill in the art.

Referring to FIGS. 12 and 13, a circuit 50 can include first and second electrodes 251, 252 that reside in communication with and closely spaced to or spaced apart from the end portions 30e of a respective channel 30, one on each side of a respective transport channel 20. The circuit 50 can include a power source 190 (e.g., a voltage source and/or current source) that can apply the electrical bias under direction of at least one processor 90p with a desired timing algorithm or timing circuit 90c. The circuit 50 can apply the voltages V1, V2, V3, V4 at the appropriate time to inject, capture or trap and transport the molecule under analysis.

FIG. 12 illustrates an optical triggering of voltage change and FIG. 13 illustrates an electrical triggering of voltage change. FIG. 13 shows that the circuit 50 can include at least one processor 90p and ammeter 60 that can monitor for ionic or tunneling current perturbations associated with an analyte in the transport channel 20 as it passes transverse electrodes 151, 152 positioned in segment $20s_1$ before the intersection I with channel 30. Part or all of the circuit 50 can reside on the device 10 (e.g., chip or substrate) or part may reside in a remote device that is connected (wired or wirelessly) to the device 10. In some embodiments, the power source 190 can releasably engage the device 10.

FIGS. 12 and 13 also illustrate that the circuit 50 can include a computer 90 with a circuit and/or at least one processor 90p that can obtain the analysis data for the analyte in the transport channel 20. The term "computer" is used broadly to include any electronic device, typically comprising at least one digital signal processor, allowing for control and communication with the circuit 50 to control operation. The computer can be local or remote from a site with the device 10.

FIG. 13 shows that the circuit 50 can include a digitizer 80 and a computer 90 with a display. These components may be combined or be discrete components. FIG. 12 also illustrates that, in some embodiments, the circuit 50 can include an imaging system 200 with a detector 220 and excitation source 205 that can take a series of images of an analyte molecule in the transport channel 20. The imaging system 200 can be any suitable imaging system. As shown, the system 200 can include an excitation light source 205 (typically for generating light that excites fluorescently labeled molecules) (which can optionally include a mirror and lens or other objective) and image generating device or detector 220 such as one or more of a camera, photomultiplier tube or photodiode. The objective/lens, where used, can reside under or over a primary surface of the device 10. The electric inputs/outputs and flow operation can reside on an opposing side of the device 10. The device 10 may also be flipped to operate on its side (with the flat primary surfaces being upright or angled) rather than substantially horizontal as shown.

In some particular embodiments, the devices 10 can be formed using the methodology described in Menard et al., *Fabrication of Sub-5 nm Nanochannels in Insulating Substrates Using Focused Ion Beam Milling*, Nano Lett. 2011, 11, 512-517 (published Dec. 20, 2010); and U.S. Provisional Patent Application Ser. No. 61/384,738, filed Sep. 21, 2010, entitled, *Methods, Systems And Devices For Forming Nanochannels*, the contents of which are hereby incorporated by reference as if recited in full herein. That is, methods of forming a fluidic analysis device can include: (a) providing a substrate having a thick overlayer; (b) milling at least two bisecting channels through the overlayer into the substrate; (c) removing the overlayer; and (d) forming at least one fluidic transport nanochannel and at least one fluidic nanochannel with a shallow segment in the substrate in response to the milling and removing steps, such that the shallow segment or integrating transverse electrodes adjacent the transport channel at an Intersection to define long and short segments of the transport channel which can be operated with significantly different field strength.

The term "thick" with reference to the overlayer means that the overlayer (e.g., the single or multi-layer structure) can have a thickness "TH" that is at least 50 nm, typically between about 50 nm to about 500 nm, and more typically between about 100 nm to about 400 nm. The overlayer can be a single monolithic material layer or may be a plurality of stacked attached layers. The overlayer can be conductive and configured to provide a desired low sputtering rate. The low sputtering rate is typically less than about 1.0 $\mu m^3/nC$, and more typically about 0.5 $\mu m^3/nC$ or less, such as for example, about 0.10 $\mu m^3/nC$, about 0.23 $\mu m^3/nC$, and about 0.30 $\mu m^3/nC$. For a single monolithic overlayer structure, the overlayer can be metallic, such as a layer comprising aluminum. The overlayer can be configured so that it is non-reactive with the substrate upper surface.

While FIB milling is described for completeness and is believed to be particularly suitable for forming the nanochannels, other embodiments are directed to other forming techniques, as described above, including, for example, electron beam lithography, nanoimprint lithography, photolithography, templating or molding strategies, and other methods understood by one of ordinary skill in the art.

Nanofluidic implementations with nanochannels are well-suited for a number of applications including single molecule detection and identification, confinement and manipulation of biopolymers, biological assays, restriction mapping of polynucleotides, DNA sizing, physical methods of genomic sequencing, and fundamental studies of the physics of confinement.

The foregoing is illustrative of the present invention and is not to be construed as limiting thereof. Although a few exemplary embodiments of this invention have been described, those skilled in the art will readily appreciate that many modifications are possible in the exemplary embodiments without materially departing from the novel teachings and advantages of this invention. Accordingly, all such modifications are intended to be included within the scope of this invention as defined in the claims. The invention is defined by the following claims, with equivalents of the claims to be included therein.

That which is claimed:

1. A method of analyzing a macromolecule, comprising:
   providing a device with at least one fluid transport nanochannel, wherein the at least one fluid transport nanochannel has an intersection that resides a distance between end portions of the at least one fluid transport nanochannel with at least one transverse fluid nanochannel with first and second segments that face each other across a width dimension of the at least one fluid transport nanochannel and are in fluid communication with the at least one fluidic transport nanochannel, each of the first and second segments of the at least one transverse fluid nanochannel in communication with a respective electrode, wherein the intersection defines a first upstream segment and a second downstream segment of the at least one fluid transport nanochannel, and wherein the second downstream segment is downstream of the first upstream segment of the at least one fluid transport nanochannel;
   injecting a macromolecule in the at least one fluid transport nanochannel;

electrically applying a bias across the first upstream segment and the second downstream segment of the at least one fluid transport nanochannel and the first and second segments of the at least one transverse fluid nanochannel during the injecting, generating different field strengths in the first upstream segment and the second downstream segment of the at least one fluid transport nanochannel;

confining the macromolecule in the at least one fluid transport nanochannel in or adjacent or in and adjacent the intersection in response to the different field strengths in the first upstream segment and the second downstream segment of the at least one fluid transport nanochannel;

controlling a molecular extension or compression of the macromolecule in the at least one fluid transport nanochannel in or adjacent the intersection or in and adjacent the intersection in response to the different field strengths in the first upstream segment and the second downstream segment of the at least one fluid transport nanochannel;

electrically removing some or all of the different field strengths causing the macromolecule to relax into an equilibrium conformation in the at least one fluid transport nanochannel in or adjacent the intersection or in and adjacent the intersection;

driving translocation of the macromolecule through the second downstream segment of the at least one fluid transport nanochannel by electrically applying a bias only along the at least one fluid transport nanochannel thereby controlling translocation of the macromolecule through the at least one fluid transport nanochannel; and analyzing the macromolecule using one or both of optical or electrical measurements of the macromolecule in the at least one fluid transport nanochannel, wherein the first upstream segment of the at least one fluid transport nanochannel has an electric field strength that is 50×-1000×greater or smaller than an electric field strength in the second downstream segment of the at least one fluid transport nanochannel during at least one of the confining the macromolecule or the controlling the molecular extension or compression of the macromolecule.

2. The method of claim 1, wherein the device comprises the at least one transverse fluid nanochannel with the first and second segments, and wherein the first and second segments of the at least one transverse fluid nanochannel are wide, shallow segments, with depths that are smaller than (i) the macromolecules' hydrodynamic sizes and (ii) the depth of the fluid transport nanochannel.

3. The method of claim 2, wherein the shallow segments merge into deeper segments, and wherein the shallow segments and the deeper segments are orthogonal to the at least one fluid transport nanochannel, the method further comprising providing fluid from reservoirs fluidically connected to the shallow segments by the deeper segments.

4. The method of claim 2, wherein the shallow segments merge into deeper segments, and wherein the deeper segments are parallel to the at least one fluid transport nanochannel.

5. The method of claims 1, wherein the device is a fluidic analysis chip, and wherein the macromolecule is a molecule of DNA, RNA, peptide, protein, or other biological or synthetic macromolecule.

6. The method of claim 1, wherein the method further comprises automatically controlling a start/stop and duration of the electrically applied biases.

7. The method of claim 6, further comprising optically detecting when the macromolecule is at a defined position in the at least one fluid transport nanochannel, then triggering an operational sequence for the electrically applied biases under direction of a timing circuit.

8. The method of claim 1, further comprising: detecting an optical or electrical triggering event associated with the macromolecule at a defined position within the at least one fluid transport nanochannel upstream of the intersection; then changing voltages of the electrically applied biases based on the detected optical or electrical triggering event to carry out the confining, the compression or extension and the driving.

9. The method of claim 1, wherein the method further comprises:

electronically detecting a voltage or current change associated with passage of the macromolecule into or in the first upstream segment of the at least one fluid transport nanochannel before the intersection; then electronically initiating an automated cycle of the applied biases for the confining, the compression or extension and the driving.

10. The method of claim 1, wherein the field strength of the first upstream segment is 50×-1000×greater than the field strength in the second downstream segment of the at least one fluid transport nanochannel during at least one of the confining of the macromolecule or the controlling the molecular compression or extension of the macromolecule.

11. The method of claim 1, wherein the first upstream segment of the at least one fluid transport nanochannel is shorter than the second downstream segment of the at least one fluid transport nanochannel.

* * * * *

UNITED STATES PATENT AND TRADEMARK OFFICE
CERTIFICATE OF CORRECTION

PATENT NO. : 10,261,065 B2
APPLICATION NO. : 14/190520
DATED : April 16, 2019
INVENTOR(S) : Ramsey et al.

It is certified that error appears in the above-identified patent and that said Letters Patent is hereby corrected as shown below:

In the Claims

Column 20, Line 11, Claim 5: Please correct "claims 1" to read -- claim 1 --

Signed and Sealed this
Thirtieth Day of July, 2019

Andrei Iancu
*Director of the United States Patent and Trademark Office*